United States Patent
Brewer et al.

(10) Patent No.: US 12,239,705 B2
(45) Date of Patent: Mar. 4, 2025

(54) THERAPEUTIC MITIGATION OF EPITHELIAL INFECTION

(71) Applicant: University of Rochester, Rochester, NY (US)

(72) Inventors: Matthew G. Brewer, Rochester, NY (US); Lisa A. Beck, Rochester, NY (US); Brian M. Ward, Rochester, NY (US); Benjamin L. Miller, Rochester, NY (US)

(73) Assignee: University of Rochester, Rochester, NY (US)

( * ) Notice: Subject to any disclaimer, the term of this patent is extended or adjusted under 35 U.S.C. 154(b) by 977 days.

(21) Appl. No.: 17/236,099

(22) Filed: Apr. 21, 2021

(65) Prior Publication Data

US 2021/0268103 A1    Sep. 2, 2021

Related U.S. Application Data

(63) Continuation-in-part of application No. PCT/US2019/056853, filed on Oct. 18, 2019.

(60) Provisional application No. 62/755,029, filed on Nov. 2, 2018.

(51) Int. Cl.
| | | |
|---|---|---|
| *A61K 39/285* | (2006.01) | |
| *A61K 31/519* | (2006.01) | |
| *A61K 39/39* | (2006.01) | |
| *A61K 45/06* | (2006.01) | |
| *C07K 16/24* | (2006.01) | |
| *C07K 16/28* | (2006.01) | |
| *A61K 39/00* | (2006.01) | |

(52) U.S. Cl.
CPC .......... *A61K 39/285* (2013.01); *A61K 31/519* (2013.01); *A61K 39/39* (2013.01); *A61K 45/06* (2013.01); *C07K 16/244* (2013.01); *C07K 16/2866* (2013.01); *A61K 2039/525* (2013.01)

(58) Field of Classification Search
None
See application file for complete search history.

(56) References Cited

U.S. PATENT DOCUMENTS

| | | |
|---|---|---|
| 2007/0259904 A1 | 11/2007 | Noronha et al. |
| 2011/0052627 A1* | 3/2011 | Chaplin .................. A61P 37/04 435/325 |
| 2016/0193203 A1 | 7/2016 | Adler et al. |
| 2016/0207995 A1 | 7/2016 | Yansura et al. |
| 2017/0067108 A1 | 3/2017 | Abbas et al. |
| 2017/0334985 A1* | 11/2017 | Wu .................. A61K 39/39591 |
| 2018/0117168 A1 | 5/2018 | Cole et al. |
| 2018/0214449 A1 | 8/2018 | Kim et al. |

(Continued)

FOREIGN PATENT DOCUMENTS

| | | |
|---|---|---|
| WO | 2010135621 A1 | 11/2010 |
| WO | 2013082476 A1 | 6/2013 |

(Continued)

OTHER PUBLICATIONS

Cotter et al. (Journal of the American Academy of Dermatology. 2018; 78 (3): S53-S62).*

(Continued)

*Primary Examiner* — Shanon A. Foley
(74) *Attorney, Agent, or Firm* — Fox Rothschild LLP

(57) ABSTRACT

This invention relates to dermatology and to treatments of infectious skin disease.

17 Claims, 11 Drawing Sheets

(56) References Cited

U.S. PATENT DOCUMENTS

2018/0224470 A1   8/2018   Leung et al.
2021/0268103 A1*  9/2021   Brewer .................. A61K 39/39

FOREIGN PATENT DOCUMENTS

| WO | 2014039461 A1 | 3/2014 |
| WO | 2017143014 A1 | 8/2017 |
| WO | 2017143270 A1 | 8/2017 |

OTHER PUBLICATIONS

Reed et al. (Clinical Infectious Diseases. 2012; 54 (6): 832-840).*
Darsow et al. (Journal of European . Journal of the European Academy of Dermatology and Venereology 30.11 (2016): 1971-1977).*
Ezeonwumelu et al. (Viruses. 2021; 13: 2379).*
Arnold et al. (International Journal of Molecular Sciences. May 25, 2023; 24 (11): 9243).*
Yuki, T. et al., "Tight Junction Proteins in Keratinocytes: Localization and Contribution to Barrier Function"; Experimental Dermatology (2007); vol. 16; pp. 324-330.
Brandner, J. M. et al., "Epidermal Tight Junctions in Health and Disease"; Tissue Barriers (2014); vol. 3:1-2; pp. e974451 (13 pgs.).
Kwon, C. W. et al., "Severe Atopic Dermatitis: Therapeutic Update"; Allergy Asthma Proceedings (2018); vol. 34; pp. 1-9.

* cited by examiner

THERAPEUTIC MITIGATION OF EPITHELIAL INFECTION

CROSS REFERENCE TO RELATED APPLICATIONS

This application is a continuation-in-part of PCT/US2019/056853, filed on Oct. 18, 2019, which claims priority to U.S. Provisional Application No. 62/755,029 filed on Nov. 2, 2018. The contents of the applications are incorporated herein by reference in their entireties.

GOVERNMENT INTERESTS

This invention was made with government support under AI117673-01 awarded by the National Institutes of Health. The government has certain rights in the invention.

FIELD OF THE INVENTION

This invention relates to dermatology and to treatments of infectious skin disease, including targeting viral infections that are initiated in the skin of atopic dermatitis patients and can become systemic leading to significant morbidity and mortality.

BACKGROUND OF THE INVENTION

Many infectious disorders, such as viral infection, have skin manifestations. Conversely, patients with skin disorders, such as atopic dermatitis (AD), often have enhanced susceptibility to viral infections of the skin. AD is the most common inflammatory skin disease. In the US, it is estimated that about 20% of children and 9% of adults suffer from AD. These patients have enhanced susceptibility to viral infections such as herpes simplex virus (HSV), vaccinia, human papilloma virus (HPV), molluscum, and coxsackie. Among them, vaccinia is the most serious, resulting in a condition called eczema vaccinatum (EV), which is lethal in up to 30% of AD patients. Currently, there is no treatment that has been shown to reduce their risk of acquiring or containing these viral infections. Ongoing clinical trials for AD patients focus primarily on ameliorating disease symptoms, but have not addressed the comorbidities that occur because of the Th2 inflammation and diseased state of the epidermis. There is a need for new treatments to mitigate skin-initiated viral infections.

SUMMARY OF INVENTION

This invention addresses the need mentioned above in a number of aspects.

In one aspect, the invention features a method of treating or preventing skin viral infection in a subject in need thereof (e.g., a subject having active AD or a history of AD). The method includes administering an effective amount of a Janus kinase (JAK) inhibitor or a Th2 pathway antagonist or both to the subject. In some embodiments, the skin viral infection can be caused by a vaccine or incidental exposure to a live virus. Examples of the vaccine include those against a disease or infection selected from the group consisting of smallpox (other orthopoxviruses), molluscum contagiosum, herpes simplex virus infection, coxsackievirus infection, and yellow fever. The viral infection can be characterized by disseminating across the skin surface and ultimately systemic as is the case for eczema vaccinatum (vaccinia virus), eczema herpeticum (herpes simplex virus) and eczema coxsackium (e.g., coxsackie virus). In one example, the method comprises administering both the JAK inhibitor and Th2 pathway antagonist to the subject. In another example, the method comprises administering the JAK inhibitor or Th2 pathway antagonist or both in combination with a live vaccine being delivered to a subject. The method is suitable for vaccines given by scarificaton of the skin, which leads to replication on the skin surface, such as yellow fever vaccine and others. The vaccine can be a smallpox vaccine, such as Dryvax, ACAM2000, MVA, LC16mO, or Copenhagen. The JAK inhibitor or Th2 pathway antagonist or both can be administered to the subject before, after or concurrent with the vaccine or a viral exposure.

Examples of the JAK inhibitor include tofacitinib, baricitinib, upadacitinib, ruxolitinib, delgocitinib, oclacitinib, filgotinib, gandotinib, lestaurtinib, momelotinib, pacritinib, PF-04965842, peficitinib, fedratinib, cucurbitacin I, pyridone 6 and CHZ868. The Th2 pathway antagonist can bind to one or more targets selected from the group consisting of the following cytokines IL-4, IL-5, IL-9, IL-13, IL-25, IL-31, IL-33 and TSLP, or a receptor thereof. The JAK inhibitor or the Th2 pathway antagonist can be a small molecule compound or a large molecule (such as an antibody or an antigen-binding portion thereof). Examples of the Th2 pathway antagonist include an antibody selected from the group consisting of dupilumab [anti-IL-4Ra], tralokinumab [anti-IL-13], lebrikizumab [anti-IL-13], nemolizumab [anti-IL-31], ANB020 [anti-IL-33], tezepelumab [anti-TSLP], mepolizumab [anti-IL-5], reslizumab [anti-IL-5], and benralizumab [anti-IL-5R]. In certain embodiments, the Th2 pathway antagonist can be an IL-4R antagonist such as an anti-IL-4R antibody or antigen-binding fragment thereof, as described herein.

In a second aspect, the invention provides a method for enhancing the safety of a vaccine. The method includes administering an effective amount of a JAK inhibitor or a Th2 pathway antagonist or both to the subject in combination with the vaccine to a subject in need thereof. The JAK inhibitor or Th2 pathway antagonist or both can be administered to the subject before, after or concurrent with the vaccine.

In another aspect, the invention provides a pharmaceutical composition for treating or preventing skin viral infection in a subject. The pharmaceutical composition contains a Janus kinase (JAK) inhibitor or a Th2 pathway antagonist or both. Also provided is a kit for treating or preventing skin viral infection in a subject. The kit contains a Janus kinase (JAK) inhibitor and/or a Th2 pathway antagonist.

In a further aspect, the invention provides a vaccine composition having a vaccine component and an adjuvant component (such as a therapeutic adjuvant component). Also provided is a kit that has a vaccine component and an adjuvant component. The adjuvant component includes one or both of a Janus kinase (JAK) inhibitor and a Th2 pathway antagonist.

In yet another aspect, the invention provides a culture system that contains cultured epithelial cells having tight junctions there between, and a culture medium containing a Th2 cytokine or a tight junction disrupting peptide (TJDP). The epithelial cells can include differentiated keratinocytes.

The culture system can be used in a screening method of identifying a candidate compound or a candidate composition for treating skin viral infection or for enhancing the safety of a vaccine. The method includes obtaining a first culture system containing epithelial cells having tight junctions therebetween; incubating the cells in a test medium containing (i) a test compound or test composition, (ii) a Th2 cytokine or a TJDP and (iii) a virus for a first period of time; and determining a replication level of the virus or a function level of the tight junctions (e.g., a transepithelial electrical resistance). The test compound or test composition is determined to be a candidate compound or a candidate composition for treating skin infection with the virus or enhancing the safety of a vaccine, if (a) the replication level is lower than a reference replication level or (b) the function level is higher than a reference function level. The reference replication level or the reference function level can be determined from a second culture system in the same manner as the first culture system except that cells in the second system are incubated in a reference medium free of the test compound or test composition. In the method and culture system described above, the culture medium, test medium, or reference medium can contain calcium.

The details of one or more embodiments of the invention are set forth in the description below. Other features, objectives, and advantages of the invention will be apparent from the description and from the claims.

Figure 1A:
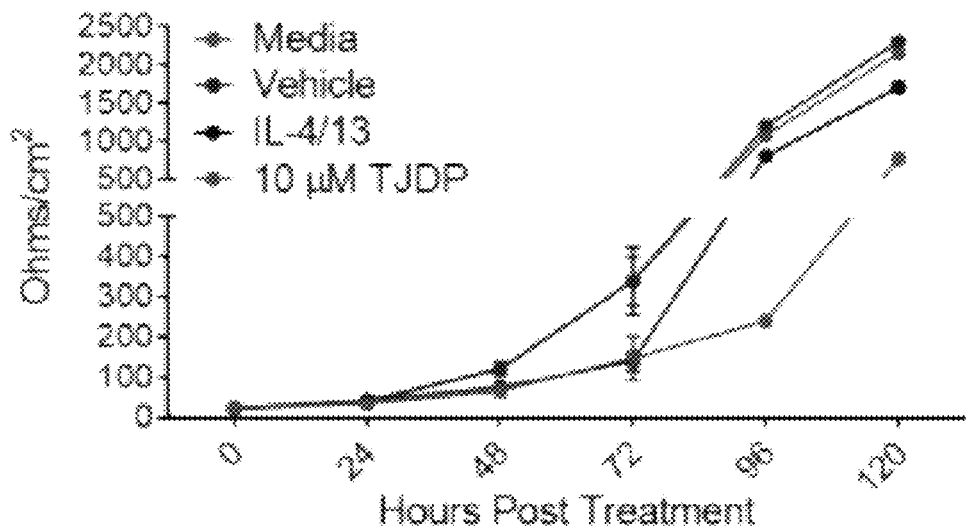
FIGS. 1A and 1B are a set of diagrams and photographs showing that barrier disruption (TJDP treatment) and Th2 cytokines (IL-4 and IL-13) enhanced vaccinia virus plaque formation in primary human foreskin keratinocytes (PHFK). Differentiating PHFK stimulated with TJDP or Th2 cytokines had reduced barrier function as measured by transepithelial electrical resistance (TER) (A) and enhanced viral infectivity (B). (A) The cells were incubated in a differentiation medium containing high concentration of calcium [1.8 mM] to induce differentiation. Concomitantly, either 10 M TJDP, Th2 cytokines (50 ng/ml each) or vehicle (0.6% DMSO/0.12% Pluronic F127) for the TJDP was added to the differentiation medium. TER was measured for 5 days with one medium change at 72 hrs. (5 days n=1, 3 days n=4). Results are represented as Ohms/cm$^2$ (Top) or values normalized to media control wells (Bottom). Error bars signify standard deviation. (B) 3 post-differentiation PHFK were infected with vaccinia virus (strain Western Reserve, 40 virions per well). PHFK monolayers were imaged 3 days post-infection (Top). On 5 days post infection, the PHFK cells were stained with crystal violet to visualize plaques (Bottom).
Figure 1A:
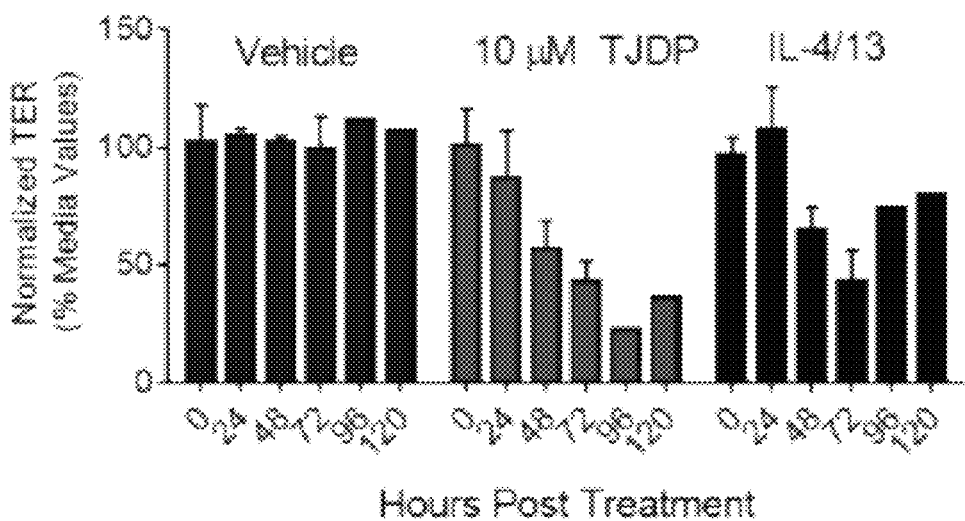

FIG. 11 is a diagram showing that pan JAK inhibition by Ruxolitinib via topical application diminished production of virus in the skin of infected animals.

DETAILED DESCRIPTION OF THE INVENTION

This invention is based, at least in part, on development of an in vitro human epidermal AD model recapitulating the two major features of atopic dermatitis (AD) or eczema disease: Th2 inflammation and epidermal barrier disruption, and unexpected discoveries of classes of molecules that mitigate one or both of these two major features.

Current estimates suggest that 20% of children and 9% of adults have AD [1]. These individuals are highly susceptible to viral skin infections including herpes simplex viruses, molluscum contagiosum (poxvirus) and of particular importance, vaccinia virus (VV). Direct or indirect exposure of AD patients to VV (in the smallpox vaccine), can lead to a disseminated, life-threatening EV, which has a mortality rate of up to 30%. VV and other Orthopoxviruses are still an important global health issue. Although smallpox has been eradicated, there are credible concerns about its use as a bioterror agent. Furthermore, a feral VV in Brazil has led to sporadic outbreaks with some infections leading to hospitalization, and one would assume such outbreaks would pose a far greater risk to the AD population [2, 3]. Therefore, if there was an orthopoxvirus outbreak in the US, such as a bioterror release of smallpox, mandatory ring vaccination procedures would result in a substantial number of AD individuals being exposed to vaccinia, causing unacceptable morbidity and mortality within that population. This invention addresses this unmet need in a number of aspects.

Viral Infection in AD, Th2 Skewed Immunity and Skin Barrier

Increased viral susceptibility in AD patients is thought to be due, at least in part, to their Th2 skewed immunity and its downstream effects such as suppressing Th1/Th17 responses, inhibiting innate immune mechanisms and disrupting barrier function [4-6].

As disclosed herein, an in vitro epidermal model of AD recapitulates two major characteristic features of the disease: Th2 inflammation (e.g., IL-4 and IL-13) and epidermal barrier disruption, which can be achieved by a peptide that disrupts TJ by blocking the homodimerization of the TJ transmembrane protein, claudin-1. Much of these observations have been made in murine models of AD where the mice were Th2 skewed either genetically or environmentally. As disclosed herein, the inventors have focused on the early events, specifically epithelial infectivity which would be the initial event in a vaccinia infection and a key determinant of total body viral load. One hypothesis is that even before the adaptive immune response develops AD patients are already at risk of developing EV because of greater epidermal infectivity. This is based on data demonstrating that human keratinocytes exposed to either Th2 cytokines or a peptide that reduces TJ barrier formation are far more susceptible to infectivity with VV. It was hypothesized that this enhanced viral permissiveness may be inhibited or mitigated by either/both Th2 blockade or JAK inhibitor treatment. The in vitro human keratinocyte model can allow one to look at the molecular events that lead to increased viral infectivity and determine whether Th2 or JAK inhibitor therapies in development for treatment of AD can reduce vaccinia infectivity. This invention disclosed herein can also allow one to identify additional lifesaving mitigators that can be administered, alone or in combination, to AD patients in the context of a mandatory smallpox vaccination campaign.

It is estimated that more than 18 million adults and an even greater number of children suffer from AD in the US. Patients with AD have a Th2-skewed adaptive immune response (that is most notable in the skin), a defect in skin barrier function, and increased susceptibility to pathogens [1]. Perturbation of skin barrier strongly associates with increased susceptibility to S. aureus colonization and widespread viral infections (e.g., HPV) [7-9]. AD patients exposed to VV (most commonly by indirect exposure to smallpox vaccinated individuals) are at risk for development of EV. Before this invention, the mechanism responsible for EV in AD patients was incompletely understood.

Skin is made of multiple layers including the epidermis, dermis and hypodermis. The epidermis has two physical barrier structures, known as the stratum corneum (SC) and tight junctions (TJ). Both of these are defective in AD patients and this defect is observed in both lesional and notably even nonlesional skin. For patients with AD, it has been hypothesized that the strong skewing of the Th2 response results in the inability of these patients to control pathogens due to a down regulation of the Th1 response, which is critical for clearing viral infections. Indeed, recombinant VV expressing Th2 cytokines has enhanced virulence in a mouse model, while expression of Th1 cytokines improves the host response [10, 11]. For example, a recombinant mousepox expressing the Th2 cytokine IL-4 resulted in high mortality of genetically resistant strains of mice and the ability to overcome cutaneous vaccination [12]. These findings are consistent with the inventors' hypothesis that exposure of the epithelium to Th2 cytokines, is in part, responsible for adverse responses to VV.

The Th2 cytokine environment of the skin within AD has been implicated as the cause of uncontrolled viral infections [6, 13]. To understand this, multiple studies have looked at cutaneous VV infections in mice. Importantly, down regulation of innate molecules, such as anti-microbial peptides released from keratinocytes have been shown to modestly enhance VV replication in mouse skin [14]. This modest effect suggests there are other factors playing a part in EV and the inventors hypothesize that some of these are epidermal-specific. SCID mice, which also show a barrier defect as measured by elevated levels of transepithelial water loss (TEWL), never survive VV infection even when treated with anti-vaccinia immunoglobulin and cidofovir (standard of care for orthopoxvirus infections). This observation suggests that epidermal barrier function may also be a critical requirement to prevent VV dissemination. Finally, one of the few studies that have attempted to replicate AD conditions looked at VV replication in an epicutaneous allergen sensitized mouse model of AD. Whereas this model showed increased viral replication and spread, the EV-like symptoms did not fully recapitulate what is seen in human patients. Accordingly, the model described in this invention is more suited for studying EV disease development in AD skin.

Individuals with AD experience enhanced susceptibility to cutaneous viral infections that in the case of VV and HSV can become systemic and are associated with increased morbidity and even mortality (VV). Importantly, no treatment is available to prevent these viral complications in AD patients. While current clinical trials focus on ameliorating signs and symptoms of AD, there are no trials addressing mitigation of serious viral complications (VV)—largely because they are so infrequent now that smallpox vaccinations are not routinely given to the general population. This highlights the need to address this concern using human in vitro and murine model systems, as disclosed herein. This approach, coupled with repurposing AD therapies that dampen Th2 pathways, provide a unique opportunity to address this serious AD health issue. This invention identifies therapeutic interventions that can reduce viral complications experienced by AD patients. This work could be lifesaving in the context of a mandatory mass ACAM2000 (live VV) vaccination effort (as would occur if smallpox was weaponized), but may also be helpful for the management of eczema herpeticum.

As described herein, the inventors developed an in vitro human epidermal AD model recapitulating the two major features of the disease. Utilizing either of these conditions, the inventors have observed remarkably enhanced vaccinia infectivity, suggesting that each of these key AD features may be responsible for making AD patients susceptible to EV.

Accordingly, one can evaluate Janus kinase inhibitors (either pan JAK inhibitors and selective JAK inhibitors) or Th2 pathway antagonist (e.g., dupilumab, tralokinumab or lebrikizumab) for abilities to reduce or eliminate epidermal viral infectivity in the in vitro model as well as in two well-established mouse AD models. Effective JAK inhibitors or Th2 pathway antagonists can be used in treatment for patients with AD. The inhibitor or antagonist, alone or in combination, can be used for prophylactic treatment of individuals with AD to augment the "state" of their skin thereby preventing viral infection in an otherwise healthy AD patient who may be exposed to viral infections. Alternatively, after infection (which is characteristic of patients with recurrent skin-based viral disease) the therapeutic implementation of the inhibitor or antagonist will be used to minimize symptoms resulting from infection.

JAK Inhibitors

One aspect of the invention provides a method of treating or preventing skin viral infection by administering an effective amount of an inhibitor of the JAK/STAT pathway to a subject who has or is at risk of having the viral infection. Also provided is a method for enhancing the safety of a vaccine. The method includes administering an effective amount of an inhibitor of the JAK/STAT pathway to a subject who will receive or has received the vaccine. The effective amount is an amount sufficient to reduce the subject's risk of the viral infection and/or mitigate the subject's at least one symptom or sign of the infection. In some embodiments, the inhibitor of the JAK/STAT pathway is an inhibitor of JAK.

Janus kinases are cytoplasmic tyrosine kinases that transduce cytokine signaling from membrane receptors to STAT transcription factors. Four JAK family members are known in the art, JAK1, JAK2, JAK3 and TYK2. Upon binding of the cytokine to its receptor, JAK family members auto- and/or transphosphorylate each other, followed by phosphorylation of STATs that then migrate to the nucleus to modulate transcription. JAK-STAT intracellular signal transduction serves the interferons, most interleukins, as well as a variety of cytokines and endocrine factors such as EPO, TPO, GH, OSM, LIF, CNTF, GM-CSF and PRL. (Vainchenker et al., 2008, Semin Cell Dev Biol. 2008 August; 19(4): 385-93). The combination of genetic models and small molecule JAK inhibitor research revealed the therapeutic potential of several JAKs. JAK3 is validated by mouse and human genetics as an immune-suppression target. (O'Shea et al., 2004).

For example, JAK3 inhibitors were successfully taken into clinical development, initially for organ transplant rejection but later also in other immuno-inflammatory indications such as rheumatoid arthritis (RA), psoriasis and Crohn's disease. TYK2 is a potential target for immuno-inflammatory diseases, validated by human genetics and mouse knockout studies. (Levy and Loomis, 2007). JAK1 is a target in the immuno-inflammatory disease area. JAK1 heterodimerizes with the other JAKs to transduce cytokine-driven pro-inflammatory signaling. Therefore, inhibition of JAK1 can be used for treating immuno-inflammatory diseases with pathology-associated cytokines that use JAK1 signaling, such as IL-6, IL-4, IL-5, IL-13, or IFNγ, as well as for other diseases driven by JAK-mediated signal transduction. JAK1 and JAK2 are implicated in intracellular signal transduction for many cytokines and hormones. Pathologies associated with any of these cytokines and hormones can be ameliorated by JAK1 and JAK2 inhibitors. Hence, several allergic or inflammatory conditions and autoimmune diseases might benefit from treatment with JAK inhibitors. See, e.g., US 20170057928.

Any kind of JAK inhibitor that is tolerated by a subject can be employed in the methods described herein. Thus, the inhibitor can be a polypeptide (such as, e.g., an anti-JAK antibody), a polynucleotide (e.g., one that encodes an inhibitory polypeptide), or a small molecule. In particular embodiments, when the inhibitor is a polynucleotide-encoded inhibitory polypeptide, the polynucleotide is introduced into the subject's cells, where the encoded polypeptide is expressed in an amount sufficient to inhibit JAK.

Inhibition of JAK can be achieved by any available means, e.g., by modulating: (1) the expression, mRNA stability, protein trafficking, modification (e.g., phosphorylation), or degradation of JAK, or (2) one or more of the normal functions of JAK. In certain embodiments, the JAK inhibitor can be, e.g., a small molecule compound or a peptide. In other embodiments, JAK inhibition is achieved by reducing the level of JAK polypeptides in the cells or inhibiting JAK function by various means that entail introducing polynucleotide inhibitors into cells. JAK levels can be reduced using, e.g., antisense, catalytic RNA/DNA, RNA interference (RNA), or "knock-out" techniques. JAK expression/function can also be inhibited using intrabodies.

In some embodiments, the JAK inhibitors are non-selective for JAKs. In other embodiments, the JAK inhibitors are selective for JAKs. Some embodiments of the invention use antagonists that are selective for all JAKs, namely pan-JAK inhibitors. An exemplary pan-JAK inhibitor is P6. Other embodiments of the invention use antagonists that are selective for one or some of JAK1, JAK2, JAK3 and TYK2, namely narrow spectrum JAK inhibitors. An exemplary narrow spectrum JAK inhibitor is JAK 1/2 inhibitor LSN 3103801 (Lilly Pharmaceuticals).

In some embodiments of the invention, the inhibitors of JAK include Baricitinib (LY3009104, INCB28050), Lestaurinib, Pacritinib (SB1518), Ruxolitinib, and Tofacitinib (tasocitinib; CP-690,550). In some embodiments of the invention, the inhibitors of JAK include AC-430, AG490, AUH-6-96, AZ-01, AZ-60, AZ960, BMS-911543, CEP-701, CEP-33779, CMP6, CP-690,550, CP-352,664, CYT387, GLPG-0634, JAK2-IA, INCB20, INCB18424, INCB028050, LS104, narrow-spectrum JAK1/2 inhibitor LSN 3103801, pan-JAK inhibitor P6, PS-608504, PS-020613, Pyridone 6, R-348, R-732, SB1518, TG101209, TG101348, WHI-PI 54, WP1066, and XL-019.

In some embodiments of the invention, the inhibitors of JAK include ortho-substituted pyrimidine compounds, imidazopyridine derivatives, heterocyclyl pyrazolopyrimidine analogues, and pyrrolo [2,3-d]pyrimidine urea compounds.

More specifically, in some embodiments, the JAK inhibitors for the invention are selective JAK1 inhibitors. Examples of selective JAK1 inhibitors are described in Norman (2012), Selective JAK1 inhibitor and selective TYK2 inhibitor patents, Expert Opinion on Therapeutic Patents, 22(10): 1233-49. Examples of JAK1 include but are not limited to: Tricylic JAK1 inhibitors by Roche in WO-2011086053; tricyclic JAK1 inhibitors by Abbott in WO-2009152133 and WO-2011068881; JAK1 inhibitors by Incyte in WO-2010135650; JAK1 inhibitors claimed by Incyte in WO-2011112662; and Anilinophthalazine-based JAK1 inhibitors by Exelixis in WO-2012037132.

In other embodiments, the JAK inhibitors suitable for the current invention are selective JAK2 inhibitors. Examples of selective JAK2 inhibitors are described in Kiss, Sayeski and Keseru (2010) Recent developments on JAK2 inhibitors: a patent review, Expert Opinion on Therapeutic Patents, 20(4): 471-495, and Dymock and See (2013), Inhibitors of JAK2 and JAK3: an update on the patent literature 2010-2012, Expert Opinion on Therapeutic Patents, early online publication (doi:10.1517/13543776.2013.765862).

Examples of selective JAK2 inhibitors include but are not limited to: Isoquinolines in WO2012030944; Pyrrolo[2,3-d]pyrimidines and quinazolines in WO2012030924, WO2012030914, WO2012030912, WO2012030910, and WO2010099379; Thieno[2,3-d]pyrimidines and pyrrolo[1,2-f][1,2,4]triazines in WO2012030894 and WO2010002472; Imidazo[2,3-c]pyridines by Array BioPharma in WO2011130146; Diaminopyrimidines and pyridines by AstraZeneca in WO2010038060 and WO2010020810; Imidazo[4,5-c]pyrrolo[2,3-b]pyridines by Bristol Meyers Squibb in WO2011028864; [1,2,4]triazolo[1,5-a]pyridine derivatives by Cephalon in WO2010141796; Pyrrolo[1,2-f][1,2,4]triazines by Cephalon in WO2010071885; Diphenylpyrrolo[1,2-f][1,2,4]triazin-2-amines by Cephalon in WO2010071885; 7,8-Dihydropyrido[4,3-d]pyrimidin-5(6H)-ones by Debiopharm-Aurigene in WO2011101806; single amino pyrazole clinical candidate 'LY2784544' by Eli Lilly in US20100152181; Triazolo[1,5-a]pyridines by Galapagos in WO2010010190 and WO2010010189; Triazolo[1,5-a]pyridines by Galapagos in WO2010010188, WO2010010187, WO2010010186 and WO2010010184; Pyrazolo[1,5-a]pyrimidines by Genentech in WO2010051549); Pyrazolo[1,5-a]pyrimidines by Genentech in WO2011003065; Pyrrolo[2,3-d]pyrimidines by Hutchison MediPharma in WO2012022045 and WO2012022265); Pyrrolo[2,3-d]pyrimidines by Incyte in WO2012068440 and WO2011028685; Pyrrolo[2,3-d]pyrimidines and other series by Incyte WO2010135621 and WO2010039939; Ruxolitinib analogues, formulations and metabolites by Incyte in WO2012068450, WO2011103423 and WO2011044481; Macrocyclic diaminopyrimidines by Incyte in WO2010085597; Pyrazoles and thiazoles by Merck in WO2010014453 and WO2010011375 and indazoles by Nerviano Medical Sciences in WO2010069966; Pyrrolo[2,3-d]pyrimidines by Pfizer in WO2011097087 WO2011075334, WO2011045702 and WO2010020905; Diaminopyrimidines by Rigel in WO2010039518, WO2010085684 and WO2010075558; compounds by TargeGen and University of Florida Research Foundation in WO2010068710.

In some embodiments, the JAK inhibitors suitable for the current invention are selective JAK3 inhibitors. Examples of selective JAK3 inhibitors are described in Wilson (2010) Expert Opinion on Therapeutic Patents, 20(5):609-23, 2013). Examples of selective JAK3 inhibitors include but are not limited to: heterocycles by Biocryst in WO2011031554, WO2011014817 and WO2011150356; Furan[2,3-d]pyrimidines by Biocryst in WO2011079230; pyrrolo[1,2-b]pyridazine by Bristol Meyers Squibb in WO2012125887; Pyrazolo[3,4-d]pyrimidines by Cellzome in WO2012022681, WO2011134831, WO2011048082, and WO2011048082; Diaminopyrimidines by Cellzome in WO2011029807; Pyrrolo[2,3-b]pyridines by Dainippon Sumitomo Pharma in JP2012012332; Diamino-pyridine-3-carboxyamides by Kowa Co. in WO2010061971; Diamino-amido-pyrimidines by Portola in WO2010129802; Diamino-pyridines by Portola in US20120108566; Diamino-pyrimidines by Rigel in WO2012015972; Pyrrolo[2,3-b]pyrazines by Roche in WO2011144584 and WO2011144585; Pyrrolo[2,3-b]pyrazines, diaminopyridines and macrocyclic compounds by Roche in WO2010063634, WO2010142752 and WO2011033053; Tricyclic naphthyridinones by Takeda in WO2010144486.

In some embodiments, the JAK inhibitors are JAK2/3 inhibitors, examples of which include but are not limited to: 3H-pyrrolo[3,2-f][1,7]naphthyridines by Advinus in WO2012127506; Various heterocycles by Almirall in WO2012069202, WO2011101161 and WO2011076419; Purin-8-ones and derivatives by Almirall in WO2011157397; Bipyridyl benzamides by Almirall in WO2012041476; Tricyclic Pyrrolopyrrolopyridines by Astellas in WO2010119875; Pyrrolo[2,3-d]pyrimidines by Japan Tobacco in WO2011013785 and macrocyclic anilino-pyrrolo[2,3-d]pyrimidines by Jiangsu Simcere in CN102617599; Pyrrolo[2,3-d]pyrimidines and pyrrolo[2,3-b]pyridines by Leo Pharma in WO2012003829 and WO2011003418; Pyrrolo[2,3-d]pyrimidines and pyrrolo[2,3-b]pyridines by Merck in WO2012054364 and WO2011137022; and Imidazo[4,5-d]pyridines and pyrazolo[2,3-a]pyridines by Palau Pharma in WO2011051452 and WO2010072823.

In other embodiments, the JAK inhibitors are selective TYK2 inhibitors. Examples of selective TYK2 inhibitors are described in Norman (2012). Examples of selective TYK2 inhibitors include but are not limited to TYK2 inhibitors by Bayer in DE-102009015070A1; TYK2 inhibitor by Roche in WO-2011113802, WO-2012035039 WO-2012066061, WO-2011113802, WO-2012035039 and WO-2012066061; Triazolopyridine TYK2 inhibitors by Cellzome in WO-2012000970; and Monocyclic TYK2 inhibitors by Cellzome in WO-2012062704.

In various embodiments, one or more JAK inhibitors, including any of those described above can be combined, i.e., administered simultaneously or sequentially, in the same or different compositions.

Th2 Pathway Antagonists

One aspect of the invention provides a method of treating or preventing skin viral infection. The method includes administering an effective amount of an inhibitor of the Th2 pathway to a subject who has or is at risk of having the viral infection. Also provided is a method for enhancing the safety of a vaccine. The method includes administering an effective amount of an inhibitor of the Th2 pathway to a subject who will receive or has received the vaccine.

Th2 cells mediate the activation and maintenance of the humoral, or antibody-mediated, immune response against extracellular parasites, bacteria, allergens, and toxins. Th2 cells mediate these functions by producing various Th2 cytokines such as IL-4, IL-5, IL-6, IL-9, IL-13, and IL-17E (IL-25) that are responsible for strong antibody production, eosinophil activation, and inhibition of several macrophage functions, thus providing phagocyte-independent protective responses. These cytokines also counteract the Th1 responses that allow for the Th2 responsiveness to IL-4. IL-4 signals through STAT6 to upregulate GATA3 expression, the master regulator of Th2 cell differentiation. Repression of this activity results in the development failure of IL-4 producing cells. IL-4 also suppresses Th1 and Th17 cell responses through the upregulation of transcriptional repressor(s) of IFNγ and IL-17 production. However, the IL-4/STAT6 pathway is not completely essential for Th2 cell differentiation as Th2 cell differentiation can also occur through other cytokines such as TSLP, IL-17E (IL-25), and IL-33. Regardless, GATA3 expression and STAT5 activation, most commonly through IL-2 for Th2 cells, is essential for Th2 cellular differentiation. See e.g., Yong-Jun Liu, et al. TSLP: An Epithelial Cell Cytokine that Regulates T Cell Differentiation by Conditioning Dendritic Cell Maturation. Annu. Rev. Immunol. 2007. 25:193-219.

Any kind of Th2 pathway antagonist that is tolerated by a subject can be employed in the methods described herein. Thus, the inhibitor can be a polypeptide (such as, e.g., an antibody), a polynucleotide (e.g., one that encodes an inhibitory polypeptide), or a small molecule. In particular embodiments, when the inhibitor is a polynucleotide-encoded inhibitory polypeptide, the polynucleotide is introduced into the subject's cells, where the encoded polypeptide is expressed in an amount sufficient to inhibit the Th2 pathway.

Inhibition of Th2 pathway can be achieved by any available means, e.g., by modulating: (1) the expression, mRNA stability, protein trafficking, modification (e.g., phosphorylation), or degradation of a Th2 cytokine or its receptor, or (2) one or more of the normal functions of the Th2 cytokine or its receptor. In certain embodiments, the Th2 pathway antagonist can be, e.g., a small molecule compound or a peptide. In other embodiments, the inhibition is achieved by reducing the level of a Th2 cytokine or its receptor polypeptide in the cells or inhibiting their function by various means that entail introducing polynucleotide inhibitors into cells. Th2 cytokine or its receptor levels can be reduced using, e.g., antisense, catalytic RNA/DNA, RNA interference (RNA), or "knock-out" techniques. The expression or function of a Th2 cytokine or its receptor can also be inhibited using intrabodies.

In some embodiments, examples of a TH2 pathway antagonist/inhibitor include inhibitors of the activity of any one of the targets selected from ITK, BTK, IL-9 (e.g., MEDI-528), IL-5 (e.g., Mepolizumab, CAS No. 196078-29-2; resilizumab), IL-13 (e.g., IMA-026, IMA-638 (also referred to as, anrukinzumab, INN No. 910649-32-0; QAX-576; IL-4/IL-13 trap), tralokinumab (also referred to as CAT-354, CAS No. 1044515-88-9); AER-001, ABT-308 (also referred to as humanized 13C5.5 antibody and lebrikizumab), IL-4 (e.g., AER-001, IL-4/IL-13 trap), OX40L, TSLP, IL-25, IL-33 and IgE (e.g., XOLAIR, QGE-031; MEDI-4212); and receptors such as: IL-9 receptor, IL-5 receptor (e.g., MEDI-563 (benralizumab, CAS No.

1044511-01-4), IL-4 receptor alpha (e.g., AMG-317, AIR-645), IL-13 receptoralpha1 (e.g., R-1671) and IL-13 receptoralpha2, OX40, TSLP-R, IL-7Ralpha (a co-receptor for TSLP), IL-17RB (receptor for IL-25), ST2 (receptor for IL-33), CCR3, CCR4, CRTH2 (e.g., AMG-853, AP768, AP-761, MLN6095, ACT129968), FeepsilonRI, Fcepsilon-RII/CD23 (receptors for IgE), Flap (e.g., GSK2190915), Syk kinase (R-343, PF3526299); CCR4 (AMG-761), TLR9 (QAX-935) and multi-cytokine inhibitor of CCR3, IL5, IL3, GM-CSF (e.g., TPI ASM8). Examples of inhibitors of the aforementioned targets are disclosed in, for example, WO2008/086395; WO2006/085938; U.S. Pat. Nos. 7,615,213; 7,501,121; WO2006/085938; WO 2007/080174; U.S. Pat. No. 7,807,788; WO2005007699; WO2007036745; WO2009/009775; WO2007/082068; WO2010/073119; WO2007/045477; WO2008/134724; US2009/0047277; and WO2008/127271.

In certain embodiments, Th2 pathway antagonist, including an IL-4R antagonist such as an anti-IL-4R antibody or antigen-binding fragment thereof, as described WO/2017/143270.

Th2 cytokines have been suggested to enhance viral susceptibility and dissemination in other organ specific in vivo models. Therefore, an alternative, uninvestigated use of TH2 pathway antagonist/inhibitor could be to mitigate skin-initiated viral infections that commonly plague AD patients. This new treatment therapy would drastically change the standard of care for individuals with AD who frequently suffer from recurrent viral skin infections, substantially decreasing their quality of life and in some cases leading to considerable morbidity and even mortality (e.g., EV).

Pharmaceutical Compositions

For research and therapeutic applications, one or more of the above-described therapeutic agents, such as a JAK inhibitor or a Th2 pathway antagonist, is generally formulated to deliver the agent to a target site in an amount sufficient to inhibit the targeted pathway protein at that site.

For example, a JAK inhibitor can be present in a pharmaceutical formulation in an amount sufficient to inhibit a Janus kinase activity at the intended site of action of one or more of JAK1, JAK2, JAK3 and TYK2, and a pharmaceutically acceptable carrier. Similarly, a Th2 pathway antagonist is present in a pharmaceutical formulation in an amount sufficient to inhibit a Th2 pathway at the intended site of action and a pharmaceutically acceptable carrier. In an example, at least one JAK inhibitor and at least one Th2 pathway antagonist are present in a same pharmaceutical formulation.

Inhibitor/antagonist compositions of the invention optionally contain other components, including, for example, a storage solution, such as a suitable buffer, e.g., a physiological buffer. In a preferred embodiment, the composition is a pharmaceutical composition and the other component is a pharmaceutically acceptable carrier, such as are described in Remington's Pharmaceutical Sciences (1980) 16th editions, Osol, ed., 1980.

A pharmaceutically acceptable carrier suitable for use in the invention is non-toxic to cells, tissues, or subjects at the dosages employed, and can include a buffer (such as a phosphate buffer, citrate buffer, and buffers made from other organic acids), an antioxidant (e.g., ascorbic acid), a low-molecular weight (less than about 10 residues) peptide, a polypeptide (such as serum albumin, gelatin, and an immunoglobulin), a hydrophilic polymer (such as polyvinylpyrrolidone), an amino acid (such as glycine, glutamine, asparagine, arginine, and/or lysine), a monosaccharide, a disaccharide, and/or other carbohydrates (including glucose, mannose, and dextrins), a chelating agent (e.g., ethylenediaminetetratacetic acid [EDTA]), a sugar alcohol (such as mannitol and sorbitol), a salt-forming counterion (e.g., sodium), and/or an anionic surfactant (such as TWEEN, PLURONICS, and PEG). In one embodiment, the pharmaceutically acceptable carrier is an aqueous pH-buffered solution.

In some embodiments of the invention, formulations of a JAK inhibitor and/or Th2 pathway antagonist suitable for oral administration are prepared as discrete units such as pills, capsules, cachets or tablets each containing a predetermined amount of an inhibitor/antagonist. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

Tablets, troches, lozenges, aqueous or oil suspensions, dispersible powders or granules, emulsions, hard or soft capsules, e.g. gelatin capsules, syrups or elixirs may be prepared for oral use. Formulations of an agent intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

In some embodiments of the invention, aqueous suspensions of a therapeutic agent contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcelluose, sodium alginate, polyvinylpyrrolidone, gum tragacanth and gum acacia, and dispersing or wetting agents such as a naturally occurring phosphatide (e.g., lecithin), a condensation product of an alkyl oxide (e.g. ethylene oxide, propylene oxide) with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxy-benzoate, one or more coloring agents, one or more flavoring agents and one or more sweetening agents, such as sucrose or saccharin.

In some embodiments of the invention, the pharmaceutical composition of a therapeutic agent is in the form of a sterile injectable preparation, such as a sterile injectable aqueous or oleaginous suspension. This suspension may be formulated according to the known art using suitable dispersing or wetting agents and suspending agents. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

Pharmaceutical compositions suitable for topical administration are useful when the desired treatment involves areas or organs readily accessible by topical application. For application topically to the skin, the pharmaceutical composition should be formulated with a suitable ointment containing the active components suspended or dissolved in a carrier. Carriers for topical administration of the particle described herein include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active particle suspended or dissolved in a carrier with suitable emulsifying agents. Suitable carriers include, but are not limited to, mineral oil, sorbitan monostearate, polysorbate 60, cetyl esters wax, cetearyl alcohol, 2-octyldodecanol, benzyl alcohol and water.

The pharmaceutical compositions described herein may also be topically applied to the lower intestinal tract by rectal suppository formulation or in a suitable enema formulation. Topically-transdermal patches are also included herein. In some embodiments of the invention, formulations for rectal administration may be presented as a suppository with a suitable base comprising for example cocoa butter or a salicylate.

In some embodiments of the invention, formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods.

Some embodiments include sustained-release pharmaceutical compositions. An exemplary sustained-release composition has a semipermeable matrix of a solid hydrophobic polymer to which a therapeutic agent is attached or in which the therapeutic agent is encapsulated. Examples of suitable polymers include a polyester, a hydrogel, a polylactide, a copolymer of L-glutamic acid and T-ethyl-L-glutamase, non-degradable ethylene-vinylacetate, a degradable lactic acid-glycolic acid copolymer, and poly-D-(−)-3-hydroxybutyric acid. Such matrices are typically in the form of shaped articles, such as films, or microcapsules. In another embodiment, a sustained-release composition includes a liposomally entrapped inhibitor. Liposomes are small vesicles composed of various types of lipids, phospholipids, and/or surfactants. These components are typically arranged in a bilayer formation, similar to the lipid arrangement of biological membranes. Liposomes containing a therapeutic agent can be prepared by known methods, such as, for example, those described in Epstein, et al. (1985) PNAS USA 82:3688-92, and Hwang, et al., (1980) PNAS USA, 77:4030-34.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 μg of the active ingredient per milliliter of solution in order that infusion of a suitable volume at a rate of about 30 mL/hr can occur.

Pharmaceutical compositions of the invention can be stored in any standard form, including, e.g., an aqueous solution or a lyophilized cake. Such compositions are typically sterile when administered to subjects. Sterilization of an aqueous solution is readily accomplished by filtration through a sterile filtration membrane. If the composition is stored in lyophilized form, the composition can be filtered before or after lyophilization and reconstitution.

Vaccine Composition

In certain embodiments, the present invention provides a vaccine composition comprising a vaccine adjuvant, wherein the vaccine adjuvant comprises a JAK inhibitor, a Th2 antagonist, or both. As used herein, the term "adjuvant" refers to any substance that acts to accelerate, prolong, or enhance antigen-specific immune responses when used in combination with specific vaccine antigens. As used herein, "a therapeutic adjuvant component" refers to any substance that provide one or more additional therapeutic or desirable effects (e.g., safety-enhancing effects, and Th2 response reduction effects) when used in combination with the specific vaccine antigens. In the context of the invention, the adjuvant or therapeutic adjuvant component (e.g., a JAK inhibitor, a Th2 antagonist) has the property of increasing the efficacy or safety or both of a vaccine in a subject, as compared to a subject that is administered the vaccine without the inhibitor or antagonist.

In certain embodiments, the use of the inhibitor or antagonist increases the safety of the administered vaccine, for example, by decreasing a related infection with vaccinia virus or the risk of an allergic reaction to a vaccine component. In certain embodiments, the use of the inhibitor or antagonist as adjuvant enables to decrease the number of administered doses of the vaccine. For example, an administration of one dose of vaccine composition with the adjuvant according to the invention is as efficient as the administration of two doses of vaccine without the adjuvant according to the invention. Similarly, an administration of one or two doses of vaccine according to the invention with the adjuvant according to the invention is as efficient as the administration of three doses of vaccine without the adjuvant according to the invention. In certain embodiments, the vaccine composition comprises a second adjuvant (e.g., alum).

The immunogen or antigen suitable for use in the vaccine compositions of the present invention may be selected from the group consisting of inactivated pathogens, attenuated pathogens, immunogenic sub-units (e.g. proteins, polypeptides, peptides, epitopes, haptens), or recombinant expression vectors, including plasmids having immunogenic inserts. In one embodiment of the present invention, the immunogen is an inactivated or killed microorganism. In certain embodiments, the vaccine composition comprises a component from a microbial organism selected from the group consisting of a smallpox vaccine (e.g., Dryvax, ACAM2000, MVA, LC16mO, or Copenhagen), influenza virus, varicella zoster virus, human immunodeficiency virus (HIV), respiratory syncytial virus (RSV), polio virus, variola virus, rabies virus, rotavirus, human papillomavirus, Ebola virus, hepatitis A virus, hepatitis B virus, hepatitis C virus, lyssavirus, measles virus, mumps virus, and Rubella virus.

Administration

Pharmaceutical compositions according to the invention are generally administered systemically. The pharmaceutical compositions described herein may be administered orally, parenterally (e.g., via intravenous, subcutaneous, intracutaneous, intramuscular, intraarticular, intraarterial, intrasynovial, intrasternal, intrathecal, intralesional or intracranial injection), topically, mucosally (e.g., rectally or vaginally), nasally, buccally, ophthalmically, via inhalation spray (e.g., delivered via nebulization, propellant or a dry powder device) or via an implanted reservoir.

The dose of an inhibitor/antagonist is sufficient to inhibit the JAK or Th2 pathway, preferably without significant toxicity. In particular in vivo embodiments, the amount of the inhibitor/antagonist is sufficient to mitigate a symptom or sign of an infection in a subject. The dose of inhibitor/antagonist depends, for example, upon the therapeutic objectives, the route of administration, the specific inhibitor/antagonist, and the condition of the subject, among other factors. Accordingly, it is necessary for the clinician to titer the dosage and modify the route of administration as required to obtain the optimal therapeutic effect. Generally, the clinician begins with a low dose and increases the dosage until the desired therapeutic effect is achieved. Starting doses for a given therapeutic agent can be extrapolated from in vitro and/or animal data.

In some embodiments, an orally administered dose of a given therapeutic agent(s) to treat human patients range from about 10 mg to about 1000 mg of the agent(s). A typical dose may be about 100 mg to about 300 mg. Thus, in various embodiments, an oral dose may contain 10, 50, 100, 125, 150, 175, 200, 225, 250, 275, 300, 350, 400, 450, 500, 550, 600, 650, 700, 750, 800, 850, 900, 950, or 1000 mg of agent(s) or any amount that falls within any ranged bounded by any of these values. A dose may be administered once a day (QD), twice per day (BID), or more frequently, depending on the pharmacokinetic and pharmacodynamic properties, including absorption, distribution, metabolism, and excretion of the particular compound. In addition, toxicity factors may influence the dosage and administration regimen. When administered orally, the pill, capsule, or tablet may be ingested daily or less frequently for a specified period of time. The regimen may be repeated for a number of cycles of therapy.

In other embodiments, the initial pharmaceutically effective amount of a therapeutic agent(s) administered per dose will be in the range of about 0.01-100 mg/kg, e.g., about 0.1 to 20 mg/kg of patient body weight per day, with an illustrative initial range of compound used being 0.3 to 15 mg/kg/day. In various embodiments, the intraperitoneal dose can be 0.01, 0.05, 0.1, 0.2, 0.3, 0.4, 0.5, 0.6, 0.7, 0.8, 1.0, 2.0, 3.0, 4.0, 5.0, 6.0, 7.0, 8.0, 9.0, 10, 11, 12, 13, 14, 15, 16, 17, 18, 19, 20, 25, 50, 75, or 100 mg/kg or any amount that falls within any ranged bounded by any of these values.

Accordingly, in one aspect, the invention provides a method of treating or preventing skin viral infection in a subject in need thereof (e.g., a subject having active AD or a history of AD) comprising administering an effective amount of a Janus kinase inhibitor or a Th2 pathway antagonist or both to the subject.

Yet in another aspect, the invention provides a method for enhancing the safety of a vaccine comprising administering an effective amount of a JAK inhibitor or a Th2 pathway antagonist or both to the subject in combination with the vaccine to a subject in need thereof. The JAK inhibitor or Th2 pathway antagonist or both can be administered to the subject before, after or concurrent with the vaccine.

Furthermore, the methods of the present invention, according to certain embodiments, comprise administering to the subject a vaccine in combination with a JAK inhibitor or a Th2 antagonist or both. As used herein, the expression "in combination with" means that the vaccine is administered before, after, or concurrent with the inhibitor or antagonist. The term "in combination with" also includes sequential or concomitant administration of an inhibitor or antagonist and a vaccine.

For example, when administered "before" the inhibitor or antagonist, the vaccine may be administered about 10, 15, or 30 minutes, or about 1, 2, 4, 6, 8, 10, 12, 24, 36, 48, 60, 72, or more than 72 hours prior to the administration of the inhibitor or antagonist. When administered "after" the inhibitor or antagonist, the vaccine may be administered about 10, 15, or 30 minutes, or about 1, 2, 4, 6, 8, 10, 12, 24, 36, 48, 60, 72, or more than 72 hours after the administration of the inhibitor or antagonist. Administration "concurrent" with the inhibitor or antagonist means that the vaccine is administered to the subject in a separate dosage form within less than 5 minutes (before, after, or at the same time) of administration of the inhibitor or antagonist, or administered to the subject as a single combined dosage formulation comprising both the vaccine and one or both of the inhibitor and antagonist.

Smallpox

The therapeutic agents and methods described in this invention are useful in treating or preventing skin viral infection. In one example, they can be used use when vaccinating AD patients in the case of a smallpox bioterrorism event—where mass vaccination would be mandated.

Smallpox has killed more people than any other infectious disease, and at a CDC meeting in 1999 it was unanimous that Smallpox posed the greatest bioterrorism threat to the United States. Since routine vaccinations ended over 45 years ago, a large proportion of the population has no immunity, which would lead to fatality rates of ~25% if Smallpox were to be released. Dryvax is no longer available; therefore, a purified version of Dryvax called ACAM2000 has been manufactured and given FDA approval for use against smallpox. Both Dryvax and ACAM2000 are live replication competent virus vaccines and as such ACAM2000 is anticipated to have the same adverse reactions as Dryvax, including EV. For fear of a clandestine release of Smallpox, the CDC has banked ACAM2000 in the Strategic National Stockpile. A mandatory mass vaccination strategy would be employed in the case of a Smallpox bioterrorism event, because vaccination within 72 hours significantly reduces mortality. In addition, mass vaccinations with ACAM2000 would also be mandated if there was a zoonotic orthopoxvirus outbreak in the US. This would put a number of populations at risk, with the AD population being the largest of these at risk groups. Therefore, the therapeutic agents and methods disclosed in this invention can be used to minimize the substantial susceptibility of AD skin to viral infection. They allow one to reduce the likelihood or severity of EV in the AD population after vaccinia inoculation without dramatically reducing the immunological protection afforded by the vaccine. This is highly desirable from a public health standpoint.

Culture system and Screening Methods

In one aspect, the invention provides an in vitro cell culture system in which two major features of AD: Th2 inflammation and epidermal barrier disruption are recapitulated. The culture system that contains cultured epithelial cells having tight junctions there between, and a culture medium containing a Th2 cytokine or a tight junction disrupting peptide. See, e.g., US 20160199440 for examples for such peptides. The epithelial cells can include differentiated keratinocytes.

This system is suitable to examine the effects of various agents on virus susceptibility of AD skin and therefore allows one to study at the molecular events that lead to increased viral infectivity and determine whether an agent (such as Th2 or JAK inhibitor) can reduce vaccinia infectivity. In one example, this system also serves as platform to screen and test various agents that could eventually be used to treat viral infection.

Accordingly, the invention provides a method of identifying a candidate compound or a candidate composition. The compound/composition thus identified can be used to treat or prevent skin viral infection, or to enhance the safety of a vaccine.

Test or candidate compounds to be screened (e.g., proteins, peptides, peptidomimetics, peptoids, antibodies, small molecules, or other drugs) can be obtained using any of the numerous approaches in combinatorial library methods known in the art. Such libraries include peptide libraries, peptoid libraries (libraries of molecules having the functionalities of peptides, but with a novel, non-peptide backbone that is resistant to enzymatic degradation); spatially addressable parallel solid phase or solution phase libraries; synthetic libraries obtained by deconvolution or affinity chromatography selection; and the "one-bead one-compound" libraries. See, e.g., Zuckermann et al. 1994, J. Med. Chem. 37:2678-2685; and Lam, 1997, Anticancer Drug Des. 12:145. Examples of methods for the synthesis of molecular libraries can be found in, e.g., DeWitt et al., 1993, PNAS USA 90:6909; Erb et al., 1994, PNAS USA 91:11422; Zuckermann et al., 1994, J. Med. Chem. 37:2678; Cho et al., 1993, Science 261:1303; Carrell et al., 1994, Angew. Chem. Int. Ed. Engl. 33:2059; Carell et al., 1994, Angew. Chem. Int. Ed. Engl. 33:2061; and Gallop et al., 1994 J. Med. Chem. 37:1233. Libraries of compounds may be presented in solution (e.g., Houghten, 1992, Biotechniques 13:412-421), or on beads (Lam, 1991, Nature 354:82-84), chips (Fodor, 1993, Nature 364:555-556), bacteria (U.S. Pat. No. 5,223,409), spores (U.S. Pat. No. 5,223,409), plasmids (Cull et al., 1992, PNAS USA 89:1865-1869), or phages (Scott and Smith 1990, Science 249:386-390; Devlin, 1990, Science 249:404-406; Cwirla et al., 1990, PNAS USA 87:6378-6382; Felici 1991, J. Mol. Biol. 222:301-310; and U.S. Pat. No. 5,223,409).

To identify a compound or composition mentioned above, one can contact or incubate a candidate compound or composition with the cell culture system in the presence of a virus of interest as disclosed herein. The cells can be epithelial cells, such as keratinocytes, derived from normal subject or an AD patient, as described in the example below. After the incubation, one then measures a replication level of the virus or a function level of the tight junctions. The level can be determined as disclosed herein or any methods known in the art. Based on the level, one can determine whether the compound or composition is effective.

Kits/Articles of Manufacture

The disclosure also provides kits for preventing or treating skin viral infection in a subject and kits for enhancing the safety of a vaccine. Such kits generally comprise one, two, or more of the JAK inhibitor, Th2 pathway antagonist, pharmaceutical composition, and vaccine composition disclosed herein, and instructions/informational material for using the kit.

In some embodiments, the kits include a carrier, package, or container that is compartmentalized to receive one or more containers such as vials, tubes, and the like, each of the container(s) including one of the separate elements to be used in a method described herein. Suitable containers include, for example, bottles, vials, syringes, and test tubes. In other embodiments, the containers are formed from a variety of materials such as glass or plastic.

The articles of manufacture provided herein generally will comprise one, two, or more of the JAK inhibitor, Th2 pathway antagonist, pharmaceutical composition, and vaccine composition disclosed herein and packaging materials. Examples of pharmaceutical packaging materials include, but are not limited to, blister packs, bottles, tubes, inhalers, pumps, bags, vials, containers, syringes, bottles, and any packaging material suitable for a selected composition and intended mode of administration and treatment.

The informational material of the kits is not limited in its form. In one embodiment, the informational material can include information about production of the JAK inhibitor, Th2 pathway antagonist, pharmaceutical composition and vaccine composition, physical properties of these agents, concentration, date of expiration, batch or production site information, and so forth. In one embodiment, the informational material relates to methods for administering the agents.

The informational material of the kits is not limited in its form. In many cases, the informational material, e.g., instructions, is provided in printed matter, e.g., a printed text, drawing, and/or photograph, e.g., a label or printed sheet. However, the informational material can also be provided in other formats, such as Braille, computer readable material, video recording, or audio recording. In another embodiment, the informational material of the kit is contact information, e.g., a physical address, email address, website, or telephone number, where a user of the kit can obtain substantive information about the active agents described herein and/or its use in the methods described herein. The informational material can also be provided in any combination of formats.

Definitions

A "Janus Kinase", or "JAK", refers to the members of a family of intracellular, non-receptor tyrosine kinases that transduce cytokine-mediated signals via the JAK-STAT pathway. The terms cover polypeptides that are identified in Genbank by the following designations, as well as polypeptides that are at least about 70% identical to polypeptides identified in Genbank by these designations: JAK1, JAK2, JAK3, and TYK2. In alternative embodiments, these terms encompass polypeptides identified in Genbank by these designations and sharing at least about 80, 90, 95, 96, 97, 98, or 99% identity.

A "STAT," "Signal Transducer and Activator of Transcription," or "Signal Transduction And Transcription" protein encompass polypeptides that are identified in Genbank by the following designations, as well as polypeptides that are at least about 70% identical to polypeptides identified in Genbank by these designations: STAT1, STAT2, STAT3, STAT4, STATS (STATSA and STATSB), and STAT6. In alternative embodiments, these terms encompass polypeptides identified in Genbank by these designations and sharing at least about 80, 90, 95, 96, 97, 98, or 99% identity.

The "JAK-STAT pathway" refers to a signal transduction pathway that typically includes three main components: (1) a receptor, (2) Janus kinase (JAK), and (3) Signal Transducer and Activator of Transcription (STAT). The receptor is activated by a signal from interferon, interleukin, growth factors, or other chemical messengers. This signal activates the kinase function of JAK, which autophosphorylates itself (phosphate groups act as "on" and "off" switches on proteins). The STAT protein then binds to the phosphorylated receptor, whereupon STAT is phosphorylated by JAK. The phosphorylated STAT protein binds to another phosphorylated STAT protein (dimerizes) and translocates into the cell nucleus. In the nucleus, the STAT protein dimer binds to DNA and promotes transcription of genes responsive to STAT.

An "inhibitor" or "antagonist" of a polypeptide or a signal transduction pathway is an agent that reduces, by any mechanism, any polypeptide action, as compared to that observed in the absence (or presence of a smaller amount) of the agent. An inhibitor of a polypeptide or a signal transduction pathway can affect: (1) the expression, mRNA stability, protein trafficking, modification (e.g., phosphorylation), or degradation of the polypeptide or a component of the signal transduction pathway, or (2) one or more of the normal functions of the polypeptide or a component of the signal transduction pathway. An inhibitor of a polypeptide or a component of the signal transduction pathway can be non-selective or selective. Preferred inhibitors/antagonists can include small or large molecules that act directly on, and are selective for, the target polypeptide.

The term "JAKs inhibitor" as used herein, refers to any naturally occurring, synthetic, or semi-synthetic compound that can inhibit the activity of one or more Janus kinases (JAKs), e.g., JAK1, JAK2, JAK3, or Tyk2. In some embodiments, the JAK inhibitor selectively inhibits the activity of only one JAK, e.g., JAK1, JAK2, JAK3, or Tyk2. In some embodiments, the JAK inhibitor can inhibit the activity of more than one JAK, e.g., JAK1 and JAK2 (e.g., ruxolitinib, baricitinib, CYT387, TG101348, AZD1480); JAK2 and JAK3; JAK1 and Tyk2; JAK2 and Tyk2; HAK3 and Tyk2. Exemplary JAK inhibitors include those described generically and specifically herein and those described in US 20180214449, US 20180117168, and US 20160193203. In some embodiments, the JAK inhibitor is ruxolitinib, baricitinib, tofacitinib, GLPG0634, GSK2586184, VX-509, lestaurtinib, INCB16562, XL019, pacritinib, CYT387, AZD1480, TG101348, NVP-BSK805, CEP33779, R-348, AC-430, CDP-R723 or BMS 911543. Additional examples include a nucleic acid, such as an antisense nucleic acid or a siRNA molecule, which targets JAK1, JAK2, JAK3, or Tyk2 RNA.

A "Th2 pathway antagonist," "Th2 pathway inhibitor," "Th2 antagonist," or "Th2 inhibitor" is an agent that inhibits the TH2 pathway. Examples of a Th2 pathway antagonist/inhibitor include inhibitors of the activity of any one of the targets selected from IL-4R antagonist (e.g., dupilumab) ITK, BTK, IL-9 (e.g., MEDI-528), IL-5 (e.g., Mepolizumab, CAS No. 196078-29-2; resilizumab), IL-13 (e.g., IMA-026, IMA-638 (also referred to as, anrukinzumab, INN No. 910649-32-0; QAX-576; IL-4/IL-13 trap), tralokinumab (also referred to as CAT-354, CAS No. 1044515-88-9); AER-001, ABT-308 (also referred to as humanized 13C5.5 antibody), IL-4 (e.g., AER-001, IL-4/IL-13 trap), OX40L, TSLP, IL-25, IL-33 and IgE (e.g., XOLAIR, QGE-031; MEDI-4212); and receptors such as: IL-9 receptor, IL-5 receptor (e.g., MEDI-563 (benralizumab, CAS No. 1044511-01-4), IL-4 receptor alpha (e.g., AMG-317, AIR-645), IL-13 receptoralpha1 (e.g., R-1671) and IL-13 receptoralpha2, OX40, TSLP-R, IL-7Ralpha (a co-receptor for TSLP), IL-17RB (receptor for IL-25), ST2 (receptor for IL-33), CCR3, CCR4, CRTH2 (e.g., AMG-853, AP768, AP-761, MLN6095, ACT129968), FcepsilonRI, FcepsilonRII/CD23 (receptors for IgE), Flap (e.g., GSK2190915), Syk kinase (R-343, PF3526299); CCR4 (AMG-761), TLR9 (QAX-935) and multi-cytokine inhibitor of CCR3, IL5, IL3, GM-CSF (e.g., TPI ASM8). Examples of inhibitors of the aforementioned targets are disclosed in, for example, WO2008/086395; WO2006/085938; U.S. Pat. Nos. 7,615, 213; 7,501,121; WO2006/085938; WO 2007/080174; U.S. Pat. No. 7,807,788; WO2005007699; WO2007036745; WO2009/009775; WO2007/082068; WO2010/073119; WO2007/045477; WO2008/134724; US2009/0047277; and WO2008/127271. Additional examples include a nucleic acid, such as an antisense nucleic acid or a siRNA molecule, which targets a component of the pathway.

As used herein, an "IL-4R antagonist," an "IL-4R inhibitor," an "IL-4Ra antagonist," an "IL-4R blocker," or an "IL-4Ra blocker," is any agent that binds to or interacts with IL-4Ra or an IL-4R ligand, and inhibits or attenuates the normal biological signaling function a type 1 and/or a type 2 IL-4 receptor. A type 1 IL-4 receptor is a dimeric receptor comprising an IL-4Ra chain and a vc chain. A type 2 IL-4 receptor is a dimeric receptor comprising an IL-4Ra chain and an IL-13Ra1 chain. Type 1 IL-4 receptors interact with and are stimulated by IL-4, while type 2 IL-4 receptors interact with and are stimulated by both IL-4 and IL-13. Thus, the IL-4R antagonists that can be used in the methods of the present invention may function by blocking IL-4-mediated signaling, IL-13-mediated signaling, or both IL-4- and IL-13-mediated signaling. The IL-4R antagonists may prevent the interaction of IL-4 and/or IL-13 with a type 1 or type 2 receptor.

The terms "polypeptide" and "protein" are used interchangeably herein to refer a polymer of amino acids, and unless otherwise limited, include atypical amino acids that can function in a similar manner to naturally occurring amino acids.

The phrases "an effective amount" and "an amount sufficient to" refer to amounts of a biologically active agent that produce an intended biological activity.

The term "antibody" as referred to herein includes whole antibodies and any antigen-binding fragment or single chains thereof. Whole antibodies are glycoproteins comprising at least two heavy (H) chains and two light (L) chains inter-connected by disulfide bonds. Each heavy chain is comprised of a heavy chain variable region (abbreviated herein as $V_H$) and a heavy chain constant region. The heavy chain constant region is comprised of three domains, $C_H1$, $C_H2$ and $C_H3$. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The heavy chain variable region CDRs and FRs are HFR1, HCDR1, HFR2, HCDR2, HFR3, HCDR3, HFR4. The light chain variable region CDRs and FRs are LFR1, LCDR1, LFR2, LCDR2, LFR3, LCDR3, LFR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (CIq) of the classical complement system.

The term "antigen-binding fragment or portion" of an antibody (or simply "antibody fragment or portion"), as used herein, refers to one or more fragments of an antibody that retain the ability to specifically bind to an antigen (e.g., IL-4 receptor or a subunit therefore). It has been shown that the antigen-binding function of an antibody can be performed by fragments of a full-length antibody. Examples of binding fragments encompassed within the term "antigen-binding fragment or portion" of an antibody include (i) a Fab fragment, a monovalent fragment consisting of the $V_L$, $V_H$, $C_L$ and $C_H1$ domains; (ii) a F(ab')2 fragment, a bivalent fragment comprising two Fab fragments linked by a disulfide bridge at the hinge region; (iii) a Fab' fragment, which is essentially an Fab with part of the hinge region (see, FUNDAMENTAL IMMUNOLOGY (Paul ed., $3^{rd}$ ed. 1993)); (iv) a Fd fragment consisting of the $V_H$ and $C_H1$ domains; (v) a Fv fragment consisting of the $V_L$ and $V_H$ domains of a single arm of an antibody, (vi) a dAb fragment (Ward et al., (1989) Nature 341:544-546), which consists of a $V_H$ domain; (vii) an isolated complementarity determining region (CDR); and (viii) a nanobody, a heavy chain variable region containing a single variable domain and two constant domains. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding fragment or portion" of an antibody. These antibody fragments are obtained using conventional techniques known to those with skill in the art, and the fragments are screened for utility in the same manner as are intact antibodies.

An "isolated antibody", as used herein, is intended to refer to an antibody that is substantially free of other antibodies having different antigenic specificities (e.g., an isolated antibody that specifically binds to an antigen is substantially free of antibodies that specifically bind antigens other than the antigen). An isolated antibody can be substantially free of other cellular material and/or chemicals.

The terms "monoclonal antibody" or "monoclonal antibody composition" as used herein refer to a preparation of antibody molecules of single molecular composition. A monoclonal antibody composition displays a single binding specificity and affinity for a particular epitope.

The term "human antibody" is intended to include antibodies having variable regions in which both the framework and CDR regions are derived from human germline immunoglobulin sequences. Furthermore, if the antibody contains a constant region, the constant region also is derived from human germline immunoglobulin sequences. The human antibodies of the invention can include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The term "human monoclonal antibody" refers to antibodies displaying a single binding specificity, which have variable regions in which both the framework and CDR regions are derived from human germline immunoglobulin sequences. In one embodiment, the human monoclonal antibodies can be produced by a hybridoma that includes a B cell obtained from a transgenic nonhuman animal, e.g., a transgenic mouse, having a genome comprising a human heavy chain transgene and a light chain transgene fused to an immortalized cell.

The term "recombinant human antibody", as used herein, includes all human antibodies that are prepared, expressed, created or isolated by recombinant means, such as (a) antibodies isolated from an animal (e.g., a mouse) that is transgenic or trans-chromosomal for human immunoglobulin genes or a hybridoma prepared therefrom (described further below), (b) antibodies isolated from a host cell transformed to express the human antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

The term "isotype" refers to the antibody class (e.g., IgM or IgG1) that is encoded by the heavy chain constant region genes. The phrases "an antibody recognizing an antigen" and "an antibody specific for an antigen" are used interchangeably herein with the term "an antibody which binds specifically to an antigen."

The term "human antibody derivatives" refers to any modified form of the human antibody, e.g., a conjugate of the antibody and another agent or antibody. The term "humanized antibody" is intended to refer to antibodies in which CDR sequences derived from the germline of another mammalian species, such as a mouse, have been grafted onto human framework sequences. Additional framework region modifications can be made within the human framework sequences.

The term "chimeric antibody" is intended to refer to antibodies in which the variable region sequences are derived from one species and the constant region sequences are derived from another species, such as an antibody in which the variable region sequences are derived from a mouse antibody and the constant region sequences are derived from a human antibody. The term can also refer to an antibody in which its variable region sequence or CDR(s) is derived from one source (e.g., an IgA1 antibody) and the constant region sequence or Fc is derived from a different source (e.g., a different antibody, such as an IgG, IgA2, IgD, IgE or IgM antibody).

As used herein, the term "affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity that reflects a 1:1 interaction between members of a binding pair (e.g., antibody and antigen). The affinity of a molecule X for its partner Y can generally be represented by the dissociation constant (KD). Affinity can be measured by common methods known in the art, including those described herein.

The term "specific binding" is defined herein as the preferential binding of binding partners to another (e.g., two polypeptides, a polypeptide and nucleic acid molecule, or two nucleic acid molecules) at specific sites. The term "specifically binds" indicates that the binding preference (e.g., affinity) for the target molecule/sequence is at least 2-fold, more preferably at least 5-fold, and most preferably at least 10- or 20-fold over a non-specific target molecule (e.g. a randomly generated molecule lacking the specifically recognized site(s)).

As used herein, an antibody that "specifically binds to" an antigen refers to an antibody that binds to an antigen but does not substantially bind to another antigen. Preferably, the antibody binds to the antigen with "high affinity", namely with a KD of $1\times10^{-7}$ M or less, more preferably $5\times10^{-8}$ M or less, more preferably $3\times10^{-8}$ M or less, more preferably $1\times10^{-8}$ M or less, more preferably $5\times10^{-9}$ M or less or even more preferably $1\times10^{-9}$ M or less. The term "does not substantially bind" to an antigen, as used herein, means does not bind or does not bind with a high affinity to the antigen, i.e. binds to the antigen with a KD of $1\times10^{-6}$ M or more, more preferably $1\times10^{-5}$ M or more, more preferably $1\times10^{-4}$ M or more, more preferably $1\times10^{-3}$ M or more, even more preferably $1\times10^{-2}$ M or more.

The term "Kassoc" or "Ka", as used herein, is intended to refer to the association rate of a particular antibody-antigen interaction, whereas the term "Kdis" or "Kd," as used herein, is intended to refer to the dissociation rate of a particular antibody-antigen interaction. The term "KD," as used herein, is intended to refer to the dissociation constant, which is obtained from the ratio of Kd to Ka (i.e., Kd/Ka) and is expressed as a molar concentration (M). KD values for antibodies can be determined using methods well established in the art. A preferred method for determining the KD of an antibody is by using surface plasmon resonance, preferably using a biosensor system such as a Biacore® system.

As used herein, an "inhibitory nucleic acid" is a double-stranded RNA, RNA interference, miRNA, siRNA, shRNA, or antisense RNA, or a portion thereof, or a mimetic thereof, that when administered to a mammalian cell results in a decrease in the expression of a target gene. Typically, a nucleic acid inhibitor comprises at least a portion of a target nucleic acid molecule, or an ortholog thereof, or comprises at least a portion of the complementary strand of a target nucleic acid molecule. Typically, expression of a target gene is reduced by 10%, 25%, 50%, 75%, or even 90-100%.

As used herein, the term "siRNA" intends a double-stranded RNA molecule that interferes with the expression of a specific gene or genes post-transcription. In some embodiments, the siRNA functions to interfere with or inhibit gene expression using the RNA interference pathway. Similar interfering or inhibiting effects may be achieved with one or more of short hairpin RNA (shRNA), microRNA (mRNA) and/or nucleic acids (such as siRNA, shRNA, or miRNA) comprising one or more modified nucleic acid residue—e.g. peptide nucleic acids (PNA), locked nucleic acids (LNA), unlocked nucleic acids (UNA), or triazole-linked DNA. Optimally, a siRNA is 18, 19, 20, 21, 22, 23 or 24 nucleotides in length and has a 2-base overhang at its 3' end. These dsRNAs can be introduced to an individual cell or culture system. Such siRNAs are used to downregulate mRNA levels or promoter activity.

"Anti-sense" refers to a nucleic acid sequence, regardless of length, that is complementary to the coding strand or mRNA of a nucleic acid sequence. Antisense RNA can be introduced to an individual cell, tissue or organanoid. An anti-sense nucleic acid can contain a modified backbone, for example, phosphorothioate, phosphorodithioate, or other modified backbones known in the art, or may contain non-natural internucleoside linkages.

As used herein, the term "subject" refers to an animal. Preferably, the animal is a mammal. A subject also refers to for example, primates (e.g., humans), cows, sheep, goats, horses, dogs, cats, rabbits, rats, mice, fish, birds and the like. In a preferred embodiment, the subject is a human.

The term "therapeutic agent" refers to any agent that is used to treat a disease. A therapeutic agent may be, for example, a polypeptide(s) (e.g., an antibody, an immunoadhesin or a peptibody), an aptamer or a small molecule that can bind to a protein or a nucleic acid molecule that can bind to a nucleic acid molecule encoding a target (i.e., siRNA), etc.

As used herein, the term "therapeutically effective amount" of a compound of the present invention refers to an amount of the compound of the present invention that will elicit the biological or medical response of a subject, or ameliorate symptoms, slow or delay disease progression, or prevent a disease, etc. In one embodiment, the term refers to the amount that inhibits or reduces microbial (e.g., viral) colonization or infection. When applied to an individual active ingredient, administered alone, the term refers to that ingredient alone. When applied to a combination, the term refers to combined amounts of the active ingredients that result in the therapeutic effect, whether administered in combination, serially or simultaneously. In one embodiment, the term refers to the individual dosage amounts or ranges of dosage amounts described in the present application.

As used herein, the term "pharmaceutically acceptable carrier or excipient" refers to a carrier medium or an excipient which does not interfere with the effectiveness of the biological activity of the active ingredient(s) of the composition and which is not excessively toxic to the host at the concentrations at which it is administered. In the context of the present invention, a pharmaceutically acceptable carrier or excipient is preferably suitable for topical formulation. The term includes, but is not limited to, a solvent, a stabilizer, a solubilizer, a tonicity enhancing agent, a structure-forming agent, a suspending agent, a dispersing agent, a chelating agent, an emulsifying agent, an anti-foaming agent, an ointment base, an emollient, a skin protecting agent, a gel-forming agent, a thickening agent, a pH adjusting agent, a preservative, a penetration enhancer, a complexing agent, a lubricant, a demulcent, a viscosity enhancer, a bio-adhesive polymer, or a combination thereof. The use of such agents for the formulation of pharmaceutically active substances is well known in the art (see, for example, "Remington's Pharmaceutical Sciences", E. W. Martin, 18th Ed., 1990, Mack Publishing Co.: Easton, PA, which is incorporated herein by reference in its entirety).

As used herein, the term "treating" or "treatment" of any disease or disorder refers in one embodiment, to ameliorating the disease or disorder (i.e., arresting or reducing the development of the disease or at least one of the clinical symptoms thereof). In another embodiment, "treating" or "treatment" refers to ameliorating at least one physical parameter, which may not be discernible by the patient. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to preventing or delaying the onset or development or progression of the disease or disorder.

As used herein, the term "a," "an," "the" and similar terms used in the context of the present invention (especially in the context of the claims) are to be construed to cover both the singular and plural unless otherwise indicated herein or clearly contradicted by the context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. No language in the specification should be construed as indicating any non-claimed element essential to the practice of the invention.

The term "small molecule" refers to an organic molecule having a molecular weight between 50 Daltons to 2500 Daltons The term "about" refers to within 10%, preferably within 5%, and more preferably within 1% of a given value or range. Alternatively, the term "about" refers to within an acceptable standard error of the mean, when considered by one of ordinary skill in the art.

EXAMPLES

Example 1

Patients with AD have increased Th2 cytokines and decreased barrier function, which is thought to make them more susceptible to infections of the skin. Taking this into account the inventors theorized that treatment of keratinocytes with Th2 cytokines or a tight junction disrupting peptide (TJDP) that reduces barrier function, should cause increased susceptibility to VV infection. To test this idea, primary human foreskin keratinocytes (PHFK) were seeded into multi-well plates and differentiated in high calcium media. Upon differentiation, cells were treated with IL-4 and IL-13, TJDP, or vehicle. Transepithelial electrical resistance (TER) was measured daily for 5 days to determine the establishment of barrier in the monolayer. It was found that skin barrier function was substantially delayed in the PHFK treated with TJDP and less so with Th2 cytokines, whereas cells treated with vehicle alone developed robust TJ within three days' post differentiation (FIG. 1A).

Figure 1B:
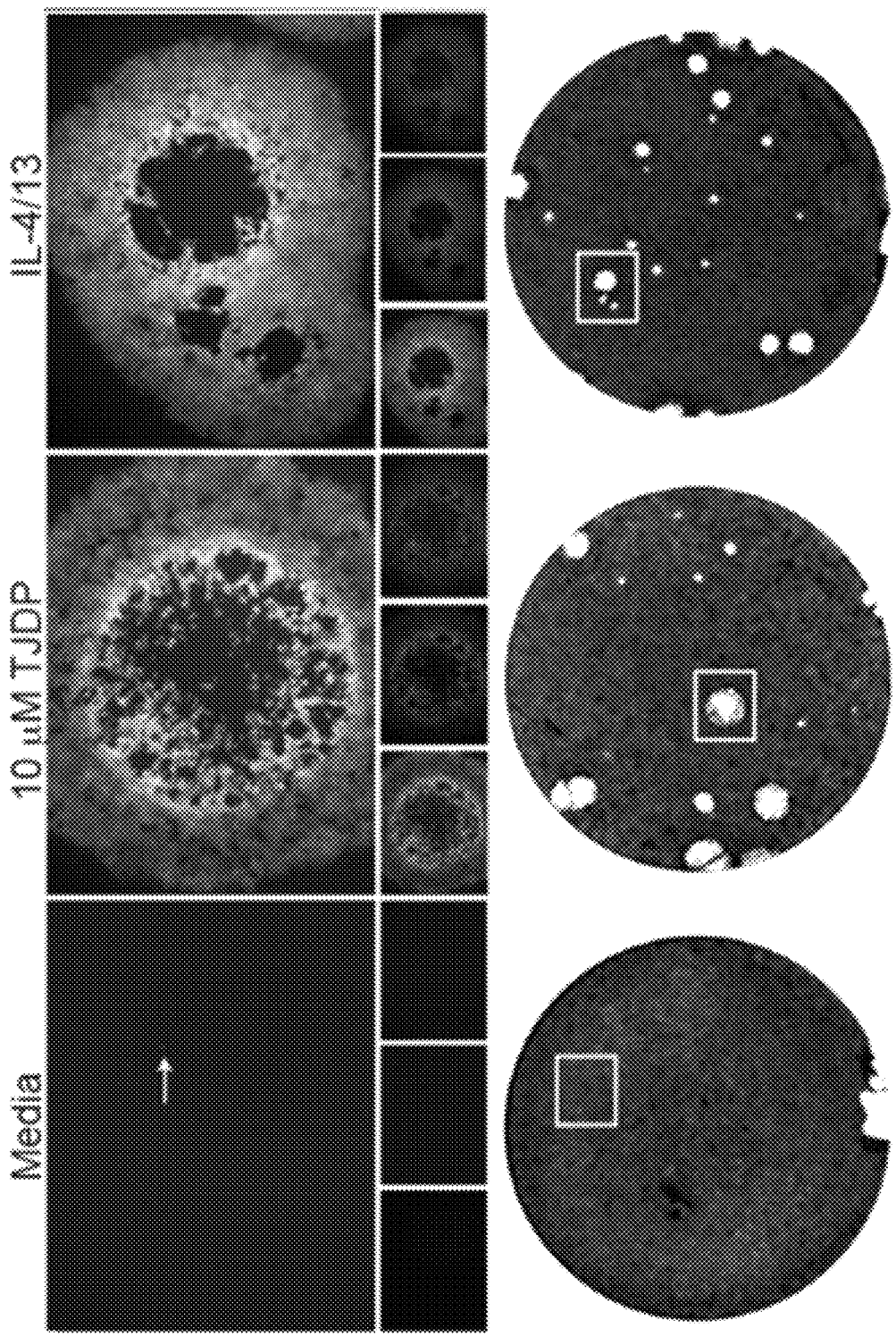
Figure 2:
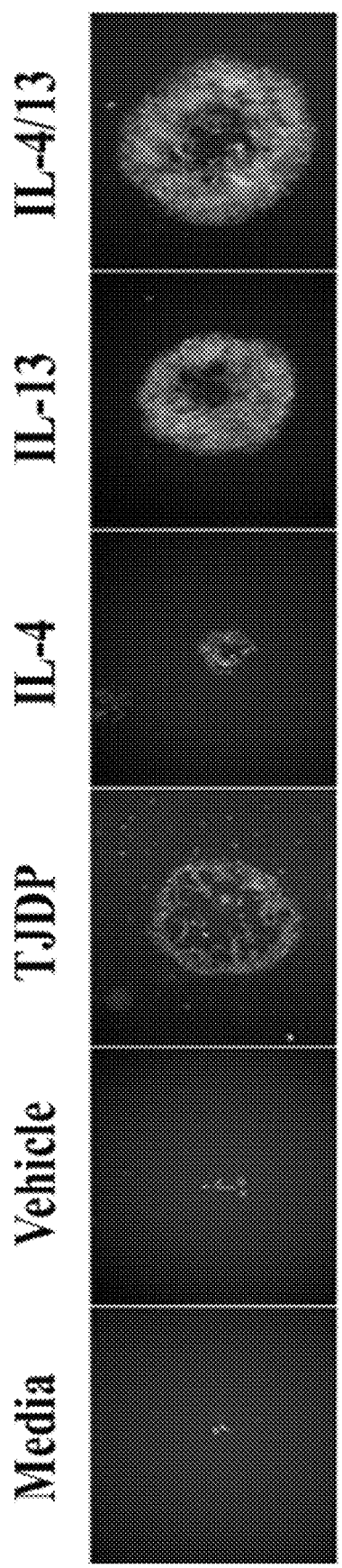
FIG. 2 is another set of photographs showing epidermal susceptibility to vaccinia virus is increased after either barrier disruption (tight junction disrupting peptide—TJDP) or exposure to Th2 cytokines (IL-4 and IL-13) compared to cells treated with vehicle (solution the TJDP is dissolved in) or media. Green and red signify infected cells with green relating to recently infected cells and red indicating late stage infection.

VV undergoes three stages of transcription: early, intermediate, and late. The reporter VV used to generate these preliminary data expressed a different fluorescent protein at each of the three stages: early (green), intermediate (red), and late (blue) respectively, and therefore viral replication can be monitored by fluorescence microscopy [16]. PHFKs were stimulated with IL-4/13 or TJDP and 3 days later infected with VV and monitored for infection status daily by fluorescence and plaque formation. Three days post infection, plaques were detected expressing all three fluorescent proteins only in the IL-4/13 or TJDP treated PHFK, indicating that these cells were fully permissive for viral replication and cell-to-cell spread which is a requirement for plaque formation (FIG. 1B Top and FIG. 2). In contrast, only individual green fluorescent cells could be detected in the untreated monolayer. These single green fluorescent cells typically did not express red or blue fluorescence, indicating that the cells were infected but virus replication did not proceed to intermediate or late gene expression.

To better visualize the extent of replication, the monolayers were stained with crystal violet to quantify the number of plaques in each treatment condition. The plaques were more numerous and larger in both the IL-4/13 and the TJDP wells compared to vehicle control (FIG. 1B Bottom). These results demonstrate that differentiated PHFK become refractory to VV infection (unlike undifferentiated PHFK), but treatments that simulate features of AD, namely Th2 cytokines or barrier disruption, significantly increase VV replication and cell-cell spread. These results provide a tractable system to study AD-like keratinocytes to study the cellular and molecular events that lead to VV susceptibility (e.g. EV) in AD patients.

Example 2

In this example, assays are carried out to address the following questions: How does the transcriptome of differentiated PHFKs change in response to TJ disruption or Th2 cytokines? Can this transcriptional change be augmented to prevent enhanced viral infection? Do the same treatments used in vitro mitigate viral disease in a mouse model of AD?

Briefly, assays are carried out to characterize the transcriptional changes that occur as a consequence of exposure to presence of Th2 cytokines (IL-4/13) or the TJDP in differentiated PHFKs focusing on gene families implicated in barrier formation (SC, TJ and lipid biology), pathogen sensing and innate immunity. Previous studies have evaluated the transcriptome of keratinocytes during differentiation and by modeling an AD setting (IL-4/13 exposure), but these were with purchased keratinocytes and no study looked at differentiated PHFK exposed to Th2 cytokines or our TJDP [17-19].

To do this, keratinocytes (6-8 donors) during differentiation are exposed to Th2 cytokines (IL-4/13) or TJDP and mRNA is isolated at multiple time points post differentiation (0, 24, 48, 72 hours). The mRNA is reverse transcribed to cDNA and examined by RNAseq analysis and bioinformatics. TER values are monitored on duplicate cultures to ensure that keratinocytes differentiate and form substantial TJ as can be determined by increases in TER over time (FIG. 1), this will be used to quality control cultures for appropriate differentiation.

Example 3

In this example, assays are carried out to determine the potential for pan- and selective-JAK inhibitors to mitigate the enhanced viral susceptibility observed in PHFKs exposed to either Th2 cytokines (IL4/IL13 alone or in combination) and/or TJDP.

To accomplish this goal, a minimum of eight PHFK donors are used to ensure that results are generalizable. Keratinocytes from these donors are used to form TJ in the presence of either Th2 cytokines or TJDP and paired cultures are exposed to JAK inhibitors, which are used at concentrations that are not cytotoxic but at doses that have been previously shown inhibit JAK signaling (tested by qPCR of relevant downstream genes). Cells are then infected with a low multiplicity of infection to observe viral dissemination (immunofluorescence) and pathogenicity (plaque formation) as described above. Additionally, JAK inhibitors are added at the time of VV infection as well as after infection (4-24 hours later) to test their therapeutic potential for mitigating already established infection. These studies are expected to (A) highlight significantly dysregulated pathways (by using JAK selective inhibitors, e.g., JAK1, JAK2, JAK3 or Tyk2) that could be important in viral susceptibility of the skin and (B) provide new therapeutic strategies to prevent or mitigate EV in AD patients.

Example 4

In this example, assays are carried out using a transgenic mouse AD model. In mice of this model, IL-13 is inducibly expressed under the epidermal-specific promoter, and keratin-5 IL-13 expression is repressed when animals are exposed to doxycycline (dox). Therefore, the animals can mature normally when dox is in their diet and then AD can be induced by its removal. This model has been shown to faithfully recapitulate human AD in clinical and molecular features as well as natural history—being born phenotypically "normal" and developing disease in "infancy" [20]. Therefore, inventors have chosen this model because it exhibits most if not all the features of human AD and the pathology is driven by the immunodominant AD Th2 cytokine (IL-13) at the level of the epidermis. After induction of AD in animals (8-10 weeks off Dox), the mice are inoculated via scarification of exposed skin with escalating doses of VV ($10^2$-$10^7$ virions) to determine the amount of virus that causes cutaneous spread of vaccinia, systemic viremia (assessed by qPCR of spleen, liver and kidneys) and even mortality. To quantify viral spread, primary and satellite skin lesions are enumerated and measured (size). Additionally, viral load is quantified by qPCR (viral polymerase) in the skin and other organs (liver, kidney, lungs) since viral dissemination is characteristic of EV in humans [21]. To link the in vivo studies to in vitro results, commercially available selective JAK inhibitors (murine homologs) are used to treat AD mice either: 1) prior to, 2) at the time of or 3) after VV inoculation to determine the prophylactic versus therapeutic potential of JAK inhibitors to mitigate EV development or severity. Endpoints are as noted above with the addition of weight loss and mortality.

Example 5

In this example, assays were carried out to examine effects of a panJAK inhibitor, Pyridone 6 (P6), on reversing keratinocyte susceptibility to viral infection and improving barrier function in keratinocytes.

Figure 3:
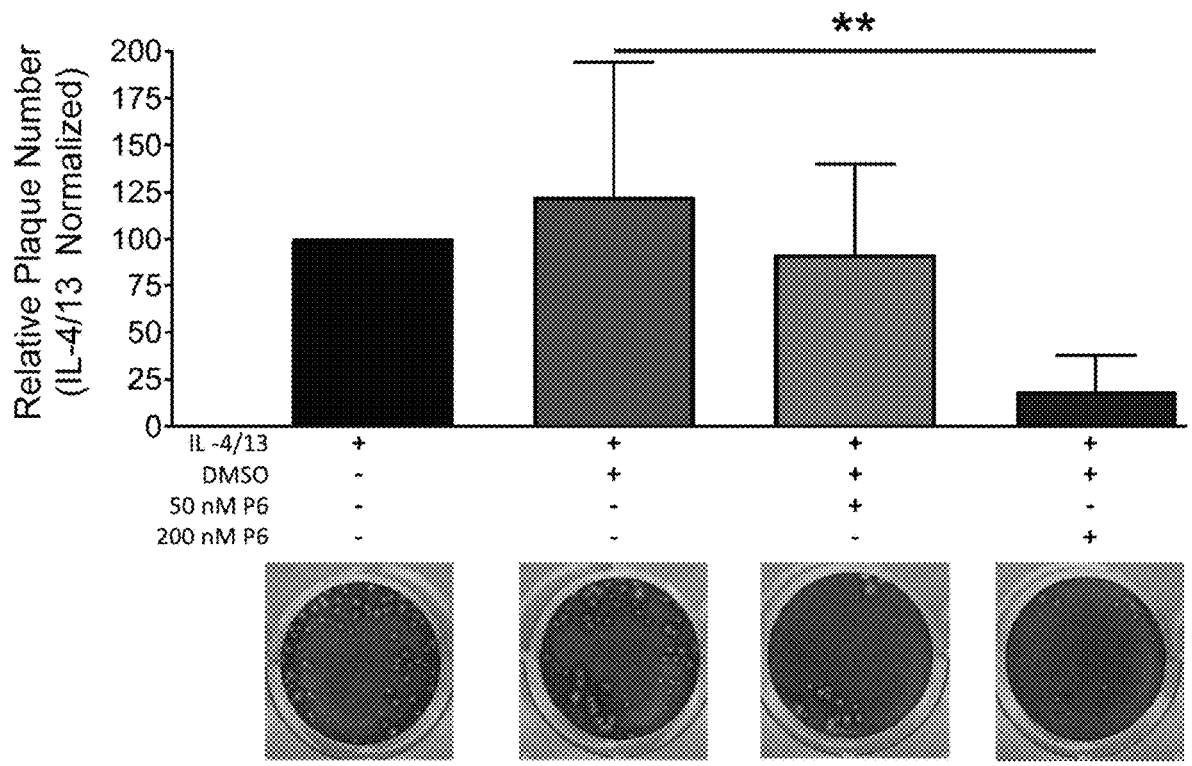
FIG. 3 is a set of diagrams and photographs showing that PanJAK inhibition mitigated vaccinia virus infection in PHFK treated with IL-4/13.

Briefly, PHFK cells were differentiated in media containing IL-4 and IL-13. Twenty-four hours later, the cells were exposed to either 50 or 200 nM of the pan-JAK inhibitor, P6, with 1% DMSO used as the vehicle control. One day later, the cells were infected with 200 pfu of VV. Three days post infection the cells were stained with crystal violet to observe plaque formation. The results were shown in FIG. 3. Shown in the top panel of FIG. 3 were plaque numbers, each of which was normalized to IL-4/13 treated controls with unadjusted values ranging from 13-90 depending on the PHFK donor (Mean+/−SD). The bottom panel showed representative images of crystal violet stained plaques. (n=7 PHFK donors; ANOVA, **$p<0.01$). These results indicated that the panJAK inhibitor P6 reversed keratinocyte susceptibility to viral infection in a dose dependent manner.

Figure 4:
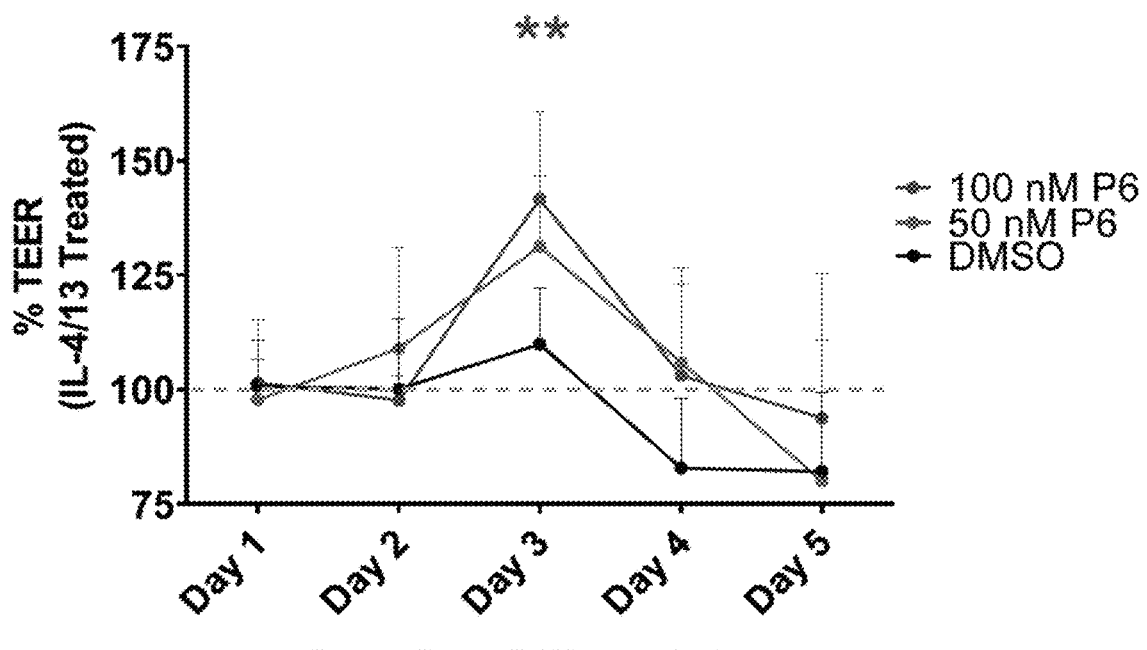
FIG. 4 is a diagram showing that PanJAK inhibition improved barrier function in PHFK treated with IL-4/13.

To examine effects of P6 on barrier function in keratinocytes, PHFK cells were differentiated in media containing IL-4 and IL-13 for two days and then treated with 50 or 100 nM of P6. One day after P6 treatment, the media was changed, removing both Th2 cytokines and JAK inhibitor. TEER was taken daily. Data was normalized to Th2 treated samples (n=5-7 donors for TEER (SEM)). Significance was tested versus a DMSO control. The results were shown in FIG. 4 (ANOVA *$p<0.05$). The results indicated that P6 improved barrier function in keratinocytes in a dose dependent manner.

Figure 5:
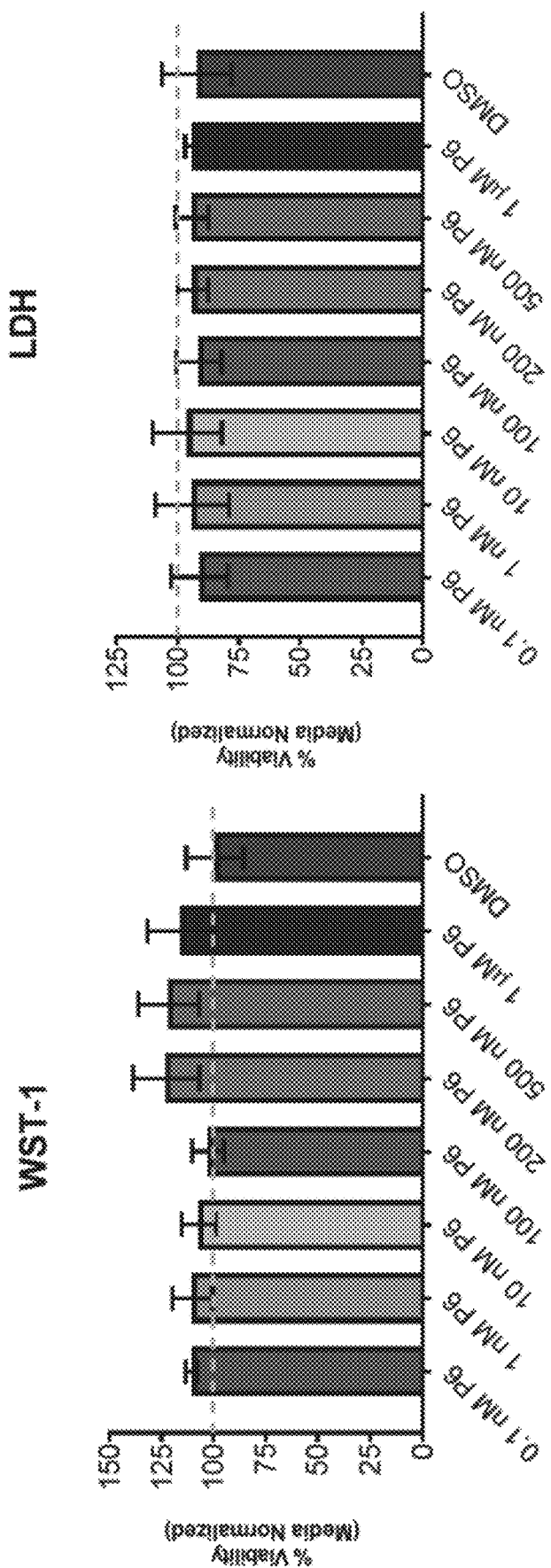
FIG. 5 is a set of diagrams showing that a panJAK inhibitor, Pyridone 6 (P6), was not toxic at 1000-fold greater concentration than the IC50.

Additional assays were carried out to examine toxicity of P6. Briefly, PHFK cells were differentiated for 2 days in the same manner described above. The cells were then treated with the P6 panJAK inhibitor at increasing concentrations. Cell viability was measured by LDH and WST-1 assay 24 hours later. As shown in FIG. 5. The results indicated that that P6 was not toxic to keratinocytes at least up to 1 µM. Further assays suggested that P6 was not toxic at 1000-fold greater concentration than the IC50s of JAK 1 (15 nM), JAK 2 (1 nM), JAK 3 (5 nM), and Tyk 2 (1 nM).

Example 6

In this example, assays were carried out to examine effects of a number of JAK inhibitors on reversing susceptibility to viral infection and improving barrier function in keratinocytes. The inhibitors included Pyridine 6, Ruxolitinib (JAK1/2 inhibitor), Abrocitinib (JAK1 inhibitor), and Ritlecitinib (JAK3 inhibitor).

Figure 6A:
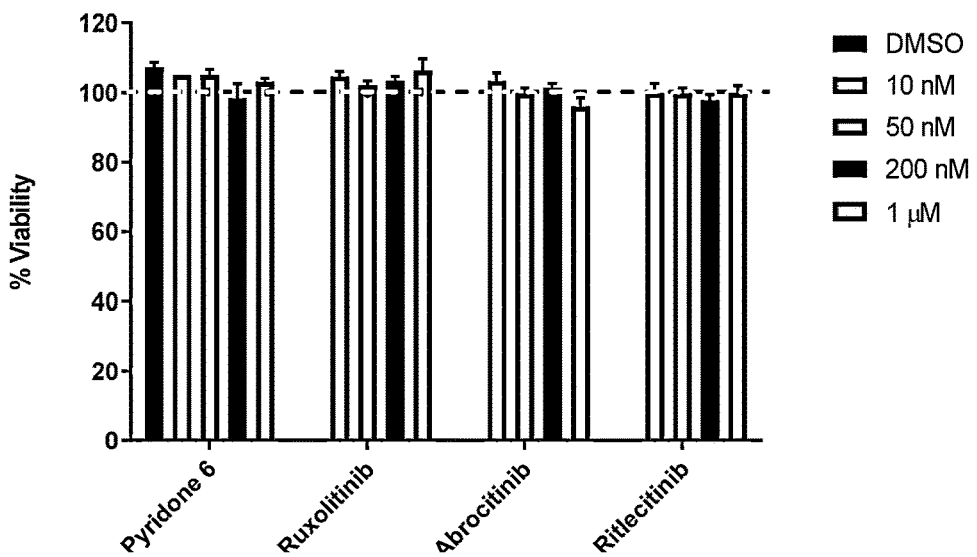
FIGS. 6A, 6B, and 6C are a set of diagrams showing that JAK inhibitors did not demonstrate toxicity over a 2-log range above reported $IC_{50}$ values at different states of differentiation: (A) undifferentiated, (B) differentiated for 1 day, and (C) differentiated for 2 days.
Figure 6B:
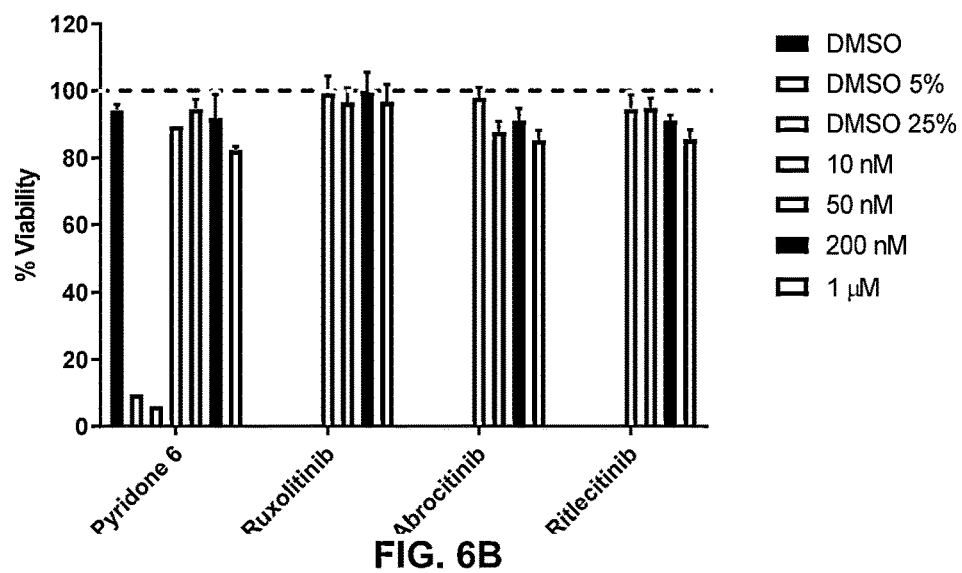
Figure 6C:
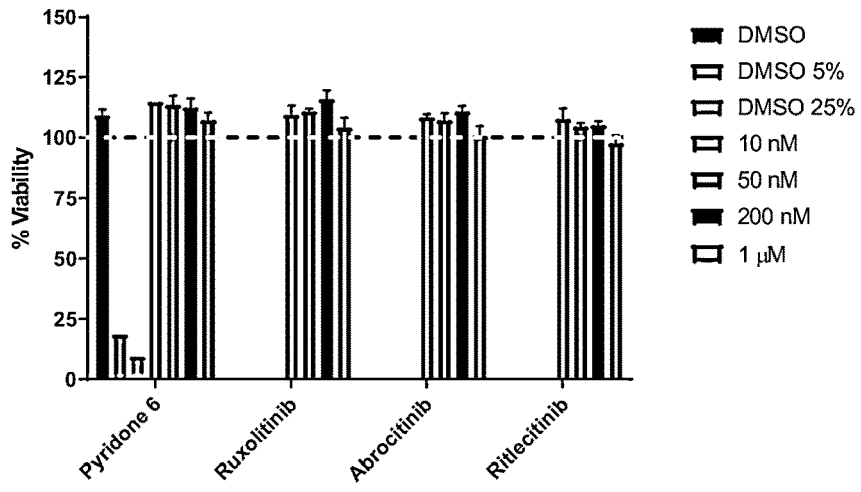

Immortalized keratinocyte N/TERT2G cells were exposed to various concentrations of Pyridine 6, Ruxolitinib, Abrocitinib, or Ritlecitinib. The cells at different states of differentiation (undifferentiated, differentiated for 1 or 2 days) were used to mimic the epidermis. After 24-hour exposure to the JAK inhibitors, the cells were screened for viability using the WST-1 assay. The results are shown in FIG. 6. All values were normalized to media treated wells (gray dashed line) and DMSO concentration (1%) was matched to the highest concentration of inhibitors used (n=3 experiments). The results indicate that the JAK inhibitors did not demonstrate toxicity over a 2-log range above the reported $IC_{50}$ values.

Figure 7:
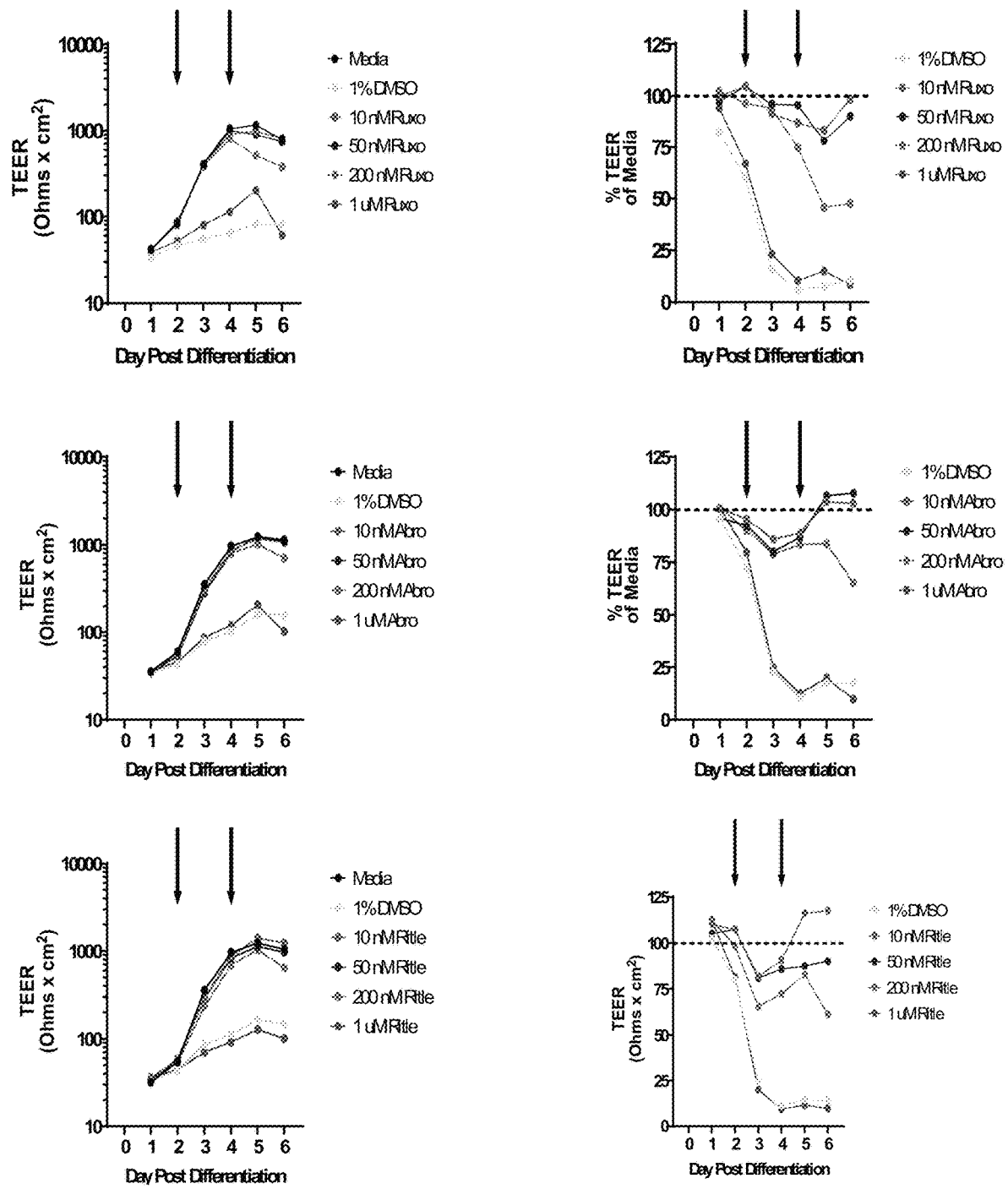
FIG. 7 is a set of diagrams showing that JAK inhibitors did not impair barrier formation at low doses.

N/TERT2G cells were differentiated in the presence of various concentrations of Pyridine 6, Ruxolitinib, Abrocitinib, or Ritlecitinib over the course of six days. Every two days the media was replaced with fresh JAK inhibitors. Transepithelial electrical resistance (TEER), a measurement of barrier function, was taken daily. The DMSO concentration (1%) was matched to the highest concentration of JAK inhibitor used. The results are shown in FIG. 7. Raw TEER values and data normalized to the media control (dashed line) is shown (n=2 experiments). The results indicate that the JAK inhibitors did not impair barrier formation at low doses.

Figure 8:
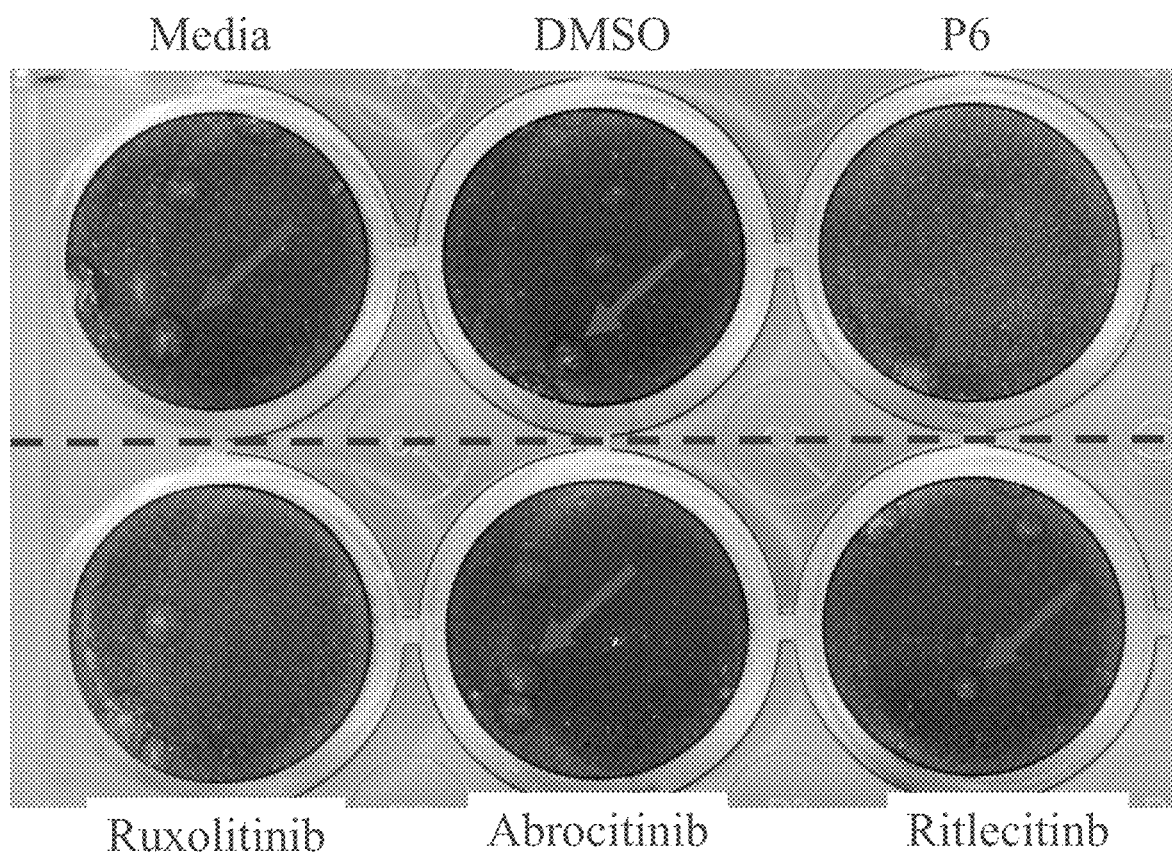
FIG. 8 is a photograph showing that neither JAK inhibitors nor DMSO enhanced keratinocyte susceptibility to vaccinia virus.

N/TERT2G cells were differentiated in the presence of 200 nM of Pyridine 6, Ruxolitinib, Abrocitinib, or Ritlecitinib. Two days post differentiation, the cells were infected with vaccinia virus (~40-60 virions). Infection was visualized 3 days post inoculation using crystal violet. The results are shown in FIG. 8, where blue arrows point at representative plaques in each condition (n=3 experiments). The results indicate that neither JAK inhibitors nor DMSO enhanced keratinocyte susceptibility to vaccinia virus.

Figure 9:
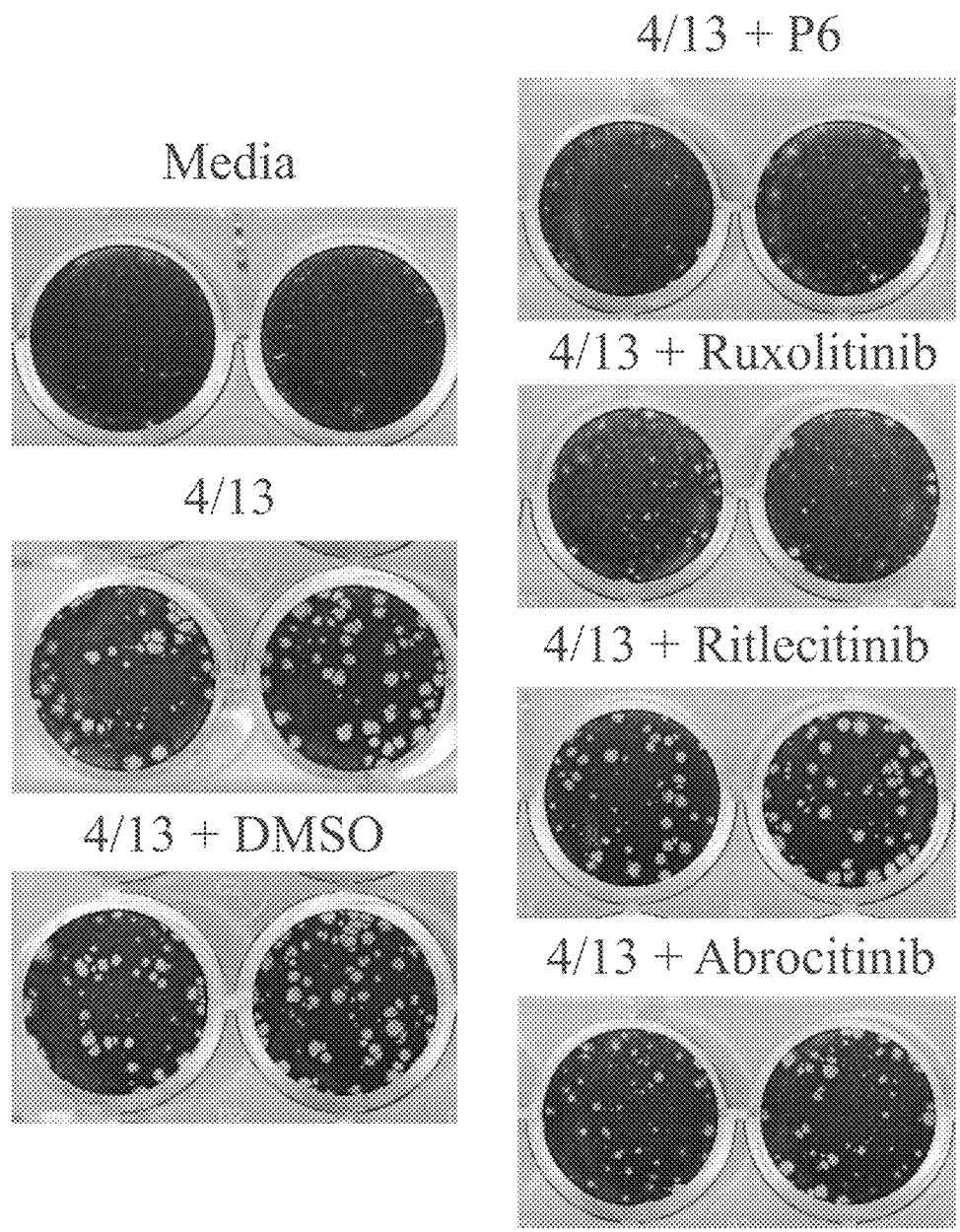
FIG. 9 is a set of photographs showing that JAK1 and 2 inhibition together diminished vaccinia virus infectivity of IL-4/13 treated keratinocyte.
Figure 10A:
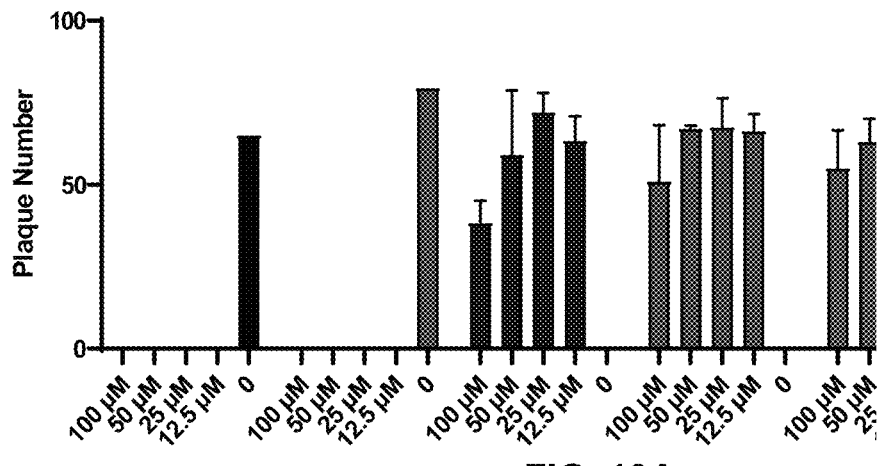
FIGS. 10A and 10B are diagrams showing that JAK1 and 2 inhibition together diminished vaccinia virus infectivity of IL-4/13 treated keratinocyte.
Figure 10B:
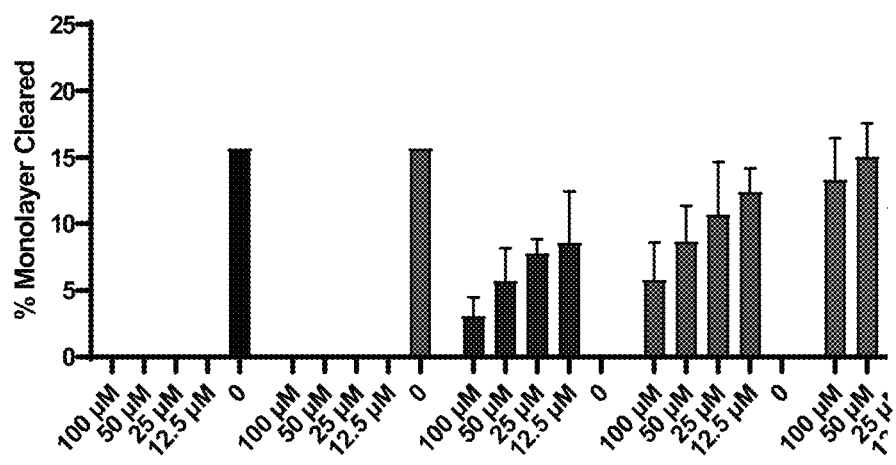

N/TERT2G cells were differentiated in the presence of IL-4 and IL-13 (50 ng/ml) or media alone. 24 hours before infection, various concentrations of Pyridine 6, Ruxolitinib, Abrocitinib, or Ritlecitinib were added to the cells. The cells were infected two days post differentiation with vaccinia virus (~40-60 virions) and infection was visualized 3 days post inoculation using crystal violet. Representative wells for each condition (FIG. 9) are shown along with quantification for plaque number and the amount of the monolayer cleared by infection (FIG. 10). The results demonstrate that JAK1 and 2 inhibition together diminished vaccinia virus infectivity of IL-4/13 treated keratinocyte.

Example 7

Figure 11:
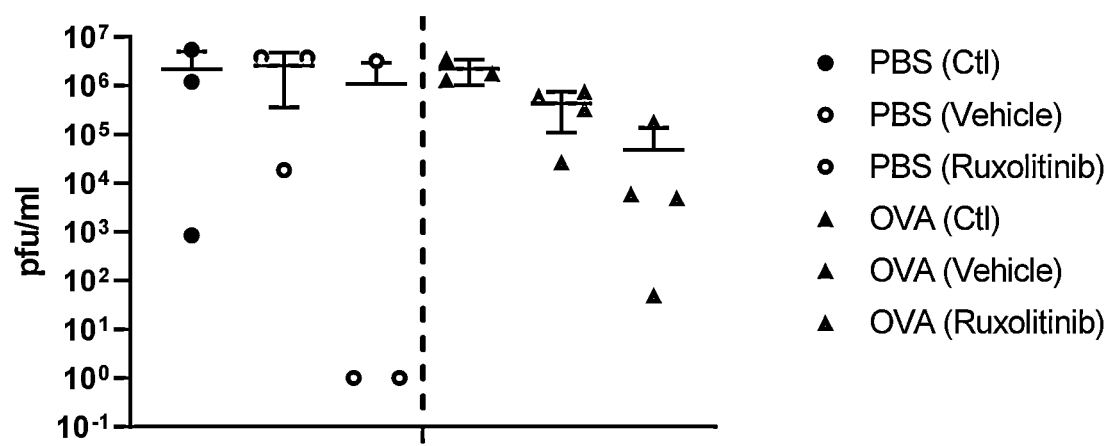

In this example, assays were carried out to examine effects of topical application of Ruxolitinib on production of virus in the skin of infected animals. PBS- or OVA-sensitized mice were treated topically with Ruxolitinib (1.5% formulation) or vehicle cream prior to cutaneous inoculation with vaccinia virus (1E6 virions). Seven days later, the animals were sacrificed and the skin was biopsied, homogenized, and screened for infectious virus using BSC40 cells. As shown in FIG. 11, JAK inhibition by Ruxolitinib via topical application diminished production of virus in the skin of infected animals.

REFERENCES

1. Weidinger, S., et al., *Atopic dermatitis*. Nat Rev Dis Primers, 2018. 4(1): p. 1.
2. Abrahao, J. S., et al., *Outbreak of severe zoonotic vaccinia virus infection, Southeastern Brazil*. Emerg Infect Dis, 2015. 21(4): p. 695-8.
3. Costa, G. B., et al., *Alternative Routes of Zoonotic Vaccinia Virus Transmission, Brazil*. Emerg Infect Dis, 2015. 21(12): p. 2244-6.
4. Oyoshi, M. K., et al., *Vaccinia virus inoculation in sites of allergic skin inflammation elicits a vigorous cutaneous IL-17 response*. Proc Natl Acad Sci USA, 2009. 106(35): p. 14954-9.
5. Oyoshi, M. K., N. Venturelli, and R. S. Geha, *Thymic stromal lymphopoietin and IL-33 promote skin inflammation and vaccinia virus replication in a mouse model of atopic dermatitis*. J Allergy Clin Immunol, 2016. 138(1): p. 283-6.
6. Howell, M. D., et al., *Cytokine milieu of atopic dermatitis skin subverts the innate immune response to vaccinia virus*. Immunity, 2006. 24(3): p. 341-8.
7. Simpson, E. L., et al., *Patients with Atopic Dermatitis Colonized with Staphylococcus aureus Have a Distinct Phenotype and Endotype*. J Invest Dermatol, 2018. 138 (10): p. 2224-2233.
8. Li, S., et al., *Altered composition of epidermal lipids correlates with Staphylococcus aureus colonization status in atopic dermatitis*. Br J Dermatol, 2017. 177(4): p. e125-e127.
9. Beck, L. A., et al., *Phenotype of atopic dermatitis subjects with a history of eczema herpeticum*. J Allergy Clin Immunol, 2009. 124(2): p. 260-9, 269 e1-7.
10. Ramshaw, I. A., et al., *Cytokines and immunity to viral infections*. Immunol Rev, 1997. 159: p. 119-35.
11. Sharma, D. P., et al., *Interleukin-4 mediates down regulation of antiviral cytokine expression and cytotoxic T-lymphocyte responses and exacerbates vaccinia virus infection in vivo*. J Virol, 1996. 70(10): p. 7103-7.
12. Jackson, R. J., et al., *Expression of mouse interleukin-4 by a recombinant ectromelia virus suppresses cytolytic lymphocyte responses and overcomes genetic resistance to mousepox*. J Virol, 2001. 75(3): p. 1205-10.
13. Liu, L., et al., *Vaccinia virus induces strong immunoregulatory cytokine production in healthy human epidermal keratinocytes: a novel strategy for immune evasion*. J Virol, 2005. 79(12): p. 7363-70.
14. Howell, M. D., et al., *Selective killing of vaccinia virus by LL-37: implications for eczema vaccinatum*. J Immunol, 2004. 172(3): p. 1763-7.
15. Oyoshi, M. K., et al., *Filaggrin deficiency promotes the dissemination of cutaneously inoculated vaccinia virus*. J Allergy Clin Immunol, 2015. 135(6): p. 1511-8 e6.
16. Dower, K., et al., *Development of Vaccinia reporter viruses for rapid, high content analysis of viral function at all stages of gene expression*. Antiviral Res, 2011. 91(1): p. 72-80.
17. Hopkin, A. S., et al., *GRHL3/GET1 and trithorax group members collaborate to activate the epidermal progenitor differentiation program*. PLoS Genet, 2012. 8(7): p. e1002829.
18. Jin, S. H., et al., *Keratinocyte-derived IL-24 plays a role in the positive feedback regulation of epidermal inflammation in response to environmental and endogenous toxic stressors*. Toxicol Appl Pharmacol, 2014. 280(2): p. 199-206.
19. Hirakawa, S., et al., *Dual oxidase 1 induced by Th2 cytokines promotes STAT6 phosphorylation via oxidative inactivation of protein tyrosine phosphatase 1B in human epidermal keratinocytes*. J Immunol, 2011. 186(8): p. 4762-70.
20. Zheng, T., et al., *Transgenic expression of interleukin-13 in the skin induces a pruritic dermatitis and skin remodeling*. J Invest Dermatol, 2009. 129(3): p. 742-51.
21. Baker, J. L. and B. M. Ward, *Development and comparison of a quantitative TaqMan-MGB real-time PCR assay to three other methods of quantifying vaccinia virions*. J Virol Methods, 2014. 196: p. 126-32.

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the scope of the invention, and all such variations are intended to be included within the scope of the following claims. All references cited herein are incorporated by reference in their entireties.

What is claimed is:

1. A method of preventing skin viral infection in a subject in need thereof, the method comprising administering an effective amount of a Janus kinase (JAK) inhibitor and a Th2 pathway antagonist to the subject,
  wherein the JAK inhibitor is selected from the group consisting of pyridone 6, abrocitinib, and ruxolitinib, and
  wherein the Th2 pathway antagonist is an antibody selected from the group consisting of dupilumab, tralokinumab, lebrikizumab, nemolizumab, etokimab, tezepelumab, mepolizumab, reslizumab, and benralizumab.

2. The method of claim 1, wherein the subject has active atopic dermatitis.

3. The method of claim 1, wherein the subject has a history of atopic dermatitis (AD).

4. The method of claim 1, wherein the skin viral infection is caused by a vaccine or vaccinia virus.

5. The method of claim 4, wherein the vaccine is against a disease or infection selected from the group consisting of smallpox, molluscum contagiosum, herpes simplex virus infection, coxsackievirus infection, and yellow fever.

6. The method of claim 1, wherein the viral infection is characterized by disseminating across the skin surface and ultimately systemic, and wherein the viral infection is eczema vaccinatum, eczema herpeticum or eczema coxsackium.

7. The method of claim 1, wherein the JAK inhibitor and Th2 pathway antagonist are administered to the subject before a viral exposure.

8. The method of claim 1, wherein the JAK inhibitor and Th2 pathway antagonist are administered to the subject after a viral exposure.

9. The method of claim 1, wherein the JAK inhibitor and Th2 pathway antagonist are administered to the subject concurrent with a viral exposure.

10. The method of claim 1, the method comprising administering the JAK inhibitor and Th2 pathway antagonist in combination with a live vaccine being delivered to a subject.

11. The method of claim 10, wherein the vaccine is a smallpox vaccine.

12. The method of claim 10, wherein the vaccine is smallpox and mpox vaccine, MVA, LC16mO, or Copenhagen.

13. The method of claim 10, wherein the JAK inhibitor and Th2 pathway antagonist are administered to the subject before the vaccine.

14. The method of claim 10, wherein the JAK inhibitor and Th2 pathway antagonist are administered to the subject after the vaccine.

15. The method of claim 10, wherein the JAK inhibitor and Th2 pathway antagonist are administered to the subject concurrent with the vaccine.

16. A pharmaceutical composition or a kit for preventing skin viral infection in a subject, comprising a Janus kinase (JAK) inhibitor and a Th2 pathway antagonist,
wherein the JAK inhibitor is selected from the group consisting of pyridone 6, abrocitinib, and ruxolitinib, and
wherein the Th2 pathway antagonist is an antibody selected from the group consisting of dupilumab, tralokinumab, lebrikizumab, nemolizumab, etokimab, tezepelumab, mepolizumab, reslizumab, and benralizumab.

17. The pharmaceutical composition or kit of claim 16, comprising
a vaccine component and
an adjuvant component having one or both of the Janus kinase (JAK) inhibitor and the Th2 pathway antagonist.

* * * * *